US011471449B2

(12) United States Patent
Geva et al.

(10) Patent No.: US 11,471,449 B2
(45) Date of Patent: *Oct. 18, 2022

(54) USE OF PRIDOPIDINE TO IMPROVE COGNITIVE FUNCTION AND FOR TREATING ALZHEIMER'S DISEASE

(71) Applicants: PRILENIA NEUROTHERAPEUTICS LTD., Herzliya (IL); THE BOARD OF REGENTS OF THE UNIVERSITY OF TEXAS SYSTEM, Austin, TX (US)

(72) Inventors: Michal Geva, Even-Yehuda (IL); Ilya Bezprozvanny, Dallas, TX (US); Merav Bassan, Ramat Gan (IL); Michael Hayden, Herzliya (IL)

(73) Assignees: Prilenia Neurotherapeutics Ltd., Herzliya (IL); The Board of Regents of the University of Texas System, Austin, TX (US)

( * ) Notice: Subject to any disclaimer, the term of this patent is extended or adjusted under 35 U.S.C. 154(b) by 43 days.

This patent is subject to a terminal disclaimer.

(21) Appl. No.: 16/591,875

(22) Filed: Oct. 3, 2019

(65) Prior Publication Data

US 2020/0093813 A1   Mar. 26, 2020

Related U.S. Application Data

(63) Continuation-in-part of application No. 15/052,368, filed on Feb. 24, 2016, now Pat. No. 10,603,311.

(60) Provisional application No. 62/186,221, filed on Jun. 29, 2015, provisional application No. 62/120,771, filed on Feb. 25, 2015.

(51) Int. Cl.
*A61P 25/08* (2006.01)
*A61K 31/451* (2006.01)
*A61P 25/28* (2006.01)
*A61K 45/06* (2006.01)

(52) U.S. Cl.
CPC ............ *A61K 31/451* (2013.01); *A61P 25/08* (2018.01); *A61P 25/28* (2018.01); *A61K 45/06* (2013.01)

(58) Field of Classification Search
CPC ....... A61K 31/451; A61K 45/06; A61P 25/08; A61P 25/28
See application file for complete search history.

(56) References Cited

U.S. PATENT DOCUMENTS

| 5,462,947 | A | 10/1995 | Andersson et al. |
|---|---|---|---|
| 6,903,120 | B2 | 6/2005 | Sonesson et al. |
| 7,417,043 | B2 | 8/2008 | Sonesson et al. |
| 7,923,459 | B2 | 4/2011 | Gauthier et al. |
| 8,809,302 | B2 | 8/2014 | Cohen et al. |
| 8,835,438 | B2 | 9/2014 | Ishiyama et al. |
| 9,006,445 | B2 | 4/2015 | Sonesson et al. |
| 9,012,476 | B2 | 4/2015 | Zimmermann et al. |
| 9,139,525 | B2 | 9/2015 | Wikstrom |
| 9,163,011 | B2 | 10/2015 | Lueoend et al. |
| RE46,117 | E | 8/2016 | Sonesson et al. |
| 9,718,805 | B2 | 8/2017 | Besidski et al. |
| 9,796,673 | B2 | 10/2017 | Wu et al. |
| 9,814,706 | B2 | 11/2017 | Zimmermann et al. |
| 10,047,049 | B2 | 8/2018 | Barel et al. |
| 10,130,621 | B2 | 11/2018 | Schmidt et al. |
| 10,322,119 | B2 * | 6/2019 | Bassan ................... A61P 25/24 |
| 10,406,145 | B2 | 9/2019 | Schmidt et al. |
| 10,603,311 | B2 * | 3/2020 | Geva ....................... A61P 25/24 |
| 2010/0048509 | A1 | 2/2010 | Kovacic et al. |
| 2011/0206782 | A1 | 8/2011 | Zhang |
| 2013/0197031 | A1 | 8/2013 | Sonesson |
| 2013/0267552 | A1 | 10/2013 | Waters et al. |
| 2014/0088140 | A1 | 3/2014 | Hayden et al. |
| 2014/0088145 | A1 | 3/2014 | Hayden et al. |
| 2015/0202302 | A1 | 7/2015 | Licht et al. |
| 2015/0209346 | A1 | 7/2015 | Hayden et al. |
| 2015/0216850 | A1 | 8/2015 | Hayden et al. |
| 2016/0095847 | A1 | 4/2016 | Sonesson et al. |
| 2016/0166559 | A1 | 6/2016 | Sonesson et al. |
| 2017/0020854 | A1 | 1/2017 | Licht et al. |
| 2017/0266170 | A1 | 9/2017 | Waters |

(Continued)

FOREIGN PATENT DOCUMENTS

| WO | WO 1999/003470 | 1/1999 |
|---|---|---|
| WO | WO 2001/046145 | 6/2001 |

(Continued)

OTHER PUBLICATIONS

Trivedi (Indian J. Psychiatry, Jan.-Mar. 2006, 48(1): 10-20, 1-21 (Year: 2006).*
Nguyen, Linda, et al. Role of sigma-1 receptors in neurodegenerative diseases. *Journal of pharmacological sciences*, 2015, 127.1: 17-29.
Pettersson, Fredrik, et al. Synthesis and evaluation of a set of 4-phenylpiperidines and 4-phenylpiperazines as D2 receptor ligands and the discovery of the dopaminergic stabilizer 4-[3-(methylsulfonyl) phenyl]-1-propylpiperidine (huntexil, pridopidine, ACR16). *Journal of medicinal chemistry*, 2010, 53.6: 2510-2520.

(Continued)

*Primary Examiner* — Sudhakar Katakam
(74) *Attorney, Agent, or Firm* — Mark S. Cohen; Pearl Cohen Zedek Latzer Baratz LLP

(57) ABSTRACT

This invention provides a method of improving cognitive function in a subject comprising periodically administering to the subject an amount of pridopidine or a pharmaceutically acceptable salt thereof effective to improve a cognitive function in the subject.
The invention also provides a method of treating a subject afflicted with Alzheimer's disease, comprising periodically administering to the subject a pharmaceutical composition comprising an amount of pridopidine or a pharmaceutically acceptable salt thereof effective to treat the subject.

17 Claims, 9 Drawing Sheets

(56) References Cited

U.S. PATENT DOCUMENTS

| | | |
|---|---|---|
| 2018/0055832 A1 | 3/2018 | Hayden et al. |
| 2018/0235950 A1 | 8/2018 | Sonesson et al. |
| 2019/0015401 A1 | 1/2019 | Sonesson |
| 2019/0046516 A1 | 2/2019 | Russ et al. |
| 2019/0192496 A1 | 6/2019 | Hayden et al. |
| 2019/0209542 A1 | 7/2019 | Licht et al. |
| 2019/0350915 A1 | 11/2019 | Bassan et al. |

FOREIGN PATENT DOCUMENTS

| | | |
|---|---|---|
| WO | WO 2006/040155 | 4/2006 |
| WO | WO 2008/127188 | 10/2008 |
| WO | WO 2009/074607 | 6/2009 |
| WO | WO 2011/107583 | 9/2011 |
| WO | WO 2012/002863 | 3/2012 |
| WO | WO 2012/028635 | 8/2012 |
| WO | WO 2013/034622 | 3/2013 |
| WO | WO 2013/086425 | 6/2013 |
| WO | WO 2013/152105 | 10/2013 |
| WO | WO 2014/205229 | 12/2014 |
| WO | WO 2015/112601 | 7/2015 |
| WO | WO 2016/003919 | 1/2016 |
| WO | WO 2016/138135 | 9/2016 |
| WO | WO 2017/015609 | 1/2017 |
| WO | WO 2017/015615 | 1/2017 |
| WO | WO 2017/048457 | 3/2017 |
| WO | WO 2017/147366 | 8/2017 |
| WO | WO 2018/039475 | 3/2018 |
| WO | WO 2018/039477 | 3/2018 |

OTHER PUBLICATIONS

A multiple-ascending dose study of pridopidine in healthy volunteers. Trial Profile, Adis Insight, Springer, Latest Information Update: May 28, 2012 (Table of Contents) (http : //adisinsight'. springer.com/trials/700207057).

Barendse, E. M., et el. (2013). Working memory deficits in high-functioning adolescents with autism spectrum disorders: neuropsychological and neuroimaging correlates. Journal of neurodevelopmental disorders, 5(1), 14.

Carlsson Research, "Carlsson Research Reports Positive Effects of ACR16 in Huntington Disease Phase II Study" Press Release, May 8, 2006.

Coyle, J. T., et al. (1983). Alzheimer's disease: a disorder of cortical cholinergic innervation. Science, 219(4589), 1184-1190.

Dahlen, Patrik. NeuroSearch provides update on the Huntexil® development programme and plans a comprehensive restructuring of the company's operations. Sep. 27, 2011.

Danysz, W., & Parsons, C. G. (2003). The NMDA receptor antagonist memantine as a symptomatological and neuroprotective treatment for Alzheimer's disease: preclinical evidence. International journal of geriatric psychiatry, 18(S1), S23-S32.

De Yebenes, J. G., et al., (2011). Pridopidine for the treatment of motor function in patients with Huntington's disease (MermaiHD): a phase 3, randomised, double-blind, placebo-controlled trial. The Lancet Neurology, 10(12), 1049-1057.

Dubinsky, R., et al. (2010). Third Annual Huntington Disease Clinical Research Symposium. Neurotherapeutics, 7(1), 135-147.

Dyhring, T., et al. (2010). The dopaminergic stabilizers pridopidine (ACR16) and (−)-OSU6162 display dopamine D2 receptor antagonism and fast receptor dissociation properties. European journal of pharmacology, 628(1-3), 19-26.

Extended European Search Report for Patent Application No. 16756274.3 dated Jul. 6, 2018.

Extended European Search Report for Patent Application No. 19191835.8 dated Nov. 12, 2019.

Grünblatt, E., et al. (1999). Potent neuroprotective and antioxidant activity of apomorphine in MPTP and 6-hydroxydopamine induced neurotoxicity. In *Advances in Research on Neurodegeneration* (pp. 57-70). Springer, Vienna.

Grünblatt, E., et al. (2000). Neuroprotective Strategies in Parkinson's Disease Using the Models of 6-Hydroxydopamine and MPTP a. *Annals of the New York Academy of Sciences*, 899(1), 262-273.

Huang, Y. C., et al. (2011). Increased prothrombin, apolipoprotein A-IV, and haptoglobin in the cerebrospinal fluid of patients with Huntington's disease. PLoS One, 6(1), e15809.

Huntington Study Group HART Investigators. (2013). A randomized, double-blind, placebo-controlled trial of pridopidine in Huntington's disease. *Movement Disorders*, 28(10), 1407-1415.

International Search Report for Patent Application No. 16756274.3 dated Jul. 6, 2018.

Johansson, B., et al. (2012). Placebo-controlled cross-over study of the monoaminergic stabiliser (−)-OSU6162 in mental fatigue following stroke or traumatic brain injury. Acta Neuropsychiatrica, 24(5), 266-274.(abstract).

Kalia, L. V., et al. (2008). NMDA receptors in clinical neurology: excitatory times ahead. *The Lancet Neurology*, 7(8), 742-755.

Lanctôt, K. L., et al. (2004). GABAergic function in Alzheimer's disease: evidence for dysfunction and potential as a therapeutic target for the treatment of behavioural and psychological symptoms of dementia. *The Canadian Journal of Psychiatry*, 49(7), 439-453.

Landwehrmeyer, B., et al. (2011). Effects of the Dopaminergic Stabilizer Pridopidine On Motor Symptoms in Huntington's Disease: A Meta-Analysis: 211. *Clinical Genetics*, 80, 48-49.

Marder, K., et al. (2000). Rate of functional decline in Huntington's disease. Neurology, 54(2), 452-452.

Michl, M., et al. (2013). Pridopidine in the pharmacological treatment of Huntington's disease. *Clinical Investigation*, 3(7), 691-699.

Millter, Marsha, "Swedish Company Announces Results of Phase II study of Dopamine Stabilizing Compound" Huntington's Disease Advocacy Center, 2006, http://www.hdac.org/features/article.php?particleNumber=254.

Mostert, J. P., et al. (2008). Therapeutic potential of fluoxetine in neurological disorders. *CNS neuroscience & therapeutics*, 14(2), 153-164.

NeuroSearch and Fleming Pederson, "NeuroSearch announces positive top-line results from Phase III Huntexil® study in Huntington's disease (the MermaiHD study)", Feb. 3, 2010.

NeuroSearch and Patrik Dahlen, NeuroSearch provides update on the Huntexil® development programme and plans a comprehensive restructuring of the company's operations. Sep. 27, 2011.

Neurosearch webite. The MermaiHD study. Apr. 2010.

NeuroSearch, "NeuroSearch A/S reports conclusions from the Multiple Ascending Dose study (MAD) with Huntexil®", May 28, 2012.

Nilsson, M., et al. (2004). The dopaminergic stabiliser ACR16 counteracts the behavioural primitivization induced by the NMDA receptor antagonist MK-801 in mice: implications for cognition. *Progress in Neuro-Psychopharmacology and Biological Psychiatry*, 28(4), 677-685.

Osterberg, O., et al. (Jan. 2013). A single-center, randomized, placebo-controlled, double-blind study to evaluate the safety, tolerability, and pharmacokinetics of multiple-ascending doses of pridopidine in healthy volunteers. In *Neurotherapeutics* (vol. 10, No. 1, pp. 175-175). 233 Spring St, New York, NY 10013 USA: Springer.

Osterberg, Ole et al. A single center, randomized, placebo controlled, double-blind study to evaluate the safety. Presented at sixth Annual Huntington Disease Clinical Research Symposium, Nov. 2012, Seattle, Washington, USA. Neurotherapeutics (2012) 9:1-17).

Rung, J. P., et al. (2005). The dopaminergic stabilizers (−)-OSU6162 and ACR16 reverse (+)-MK-801-induced social withdrawal in rats. *Progress in Neuro-Psychopharmacology and Biological Psychiatry*, 29(5), 833-839.

Rung, J. P., et al. (2011). Effects of the dopamine stabilizers (S)-(−)-OSU6162 and ACR16 on prolactin secretion in drug-naive and monoamine-depleted rats. *Naunyn-Schmiedeberg's archives of pharmacology*, 384(1), 39-45.

Sahlholm, K., et al. (2013). The dopamine stabilizers ACR16 and (−)-OSU6162 display nanomolar affinities at the σ-1 receptor. *Molecular psychiatry*, 18(1), 12.

(56) References Cited

OTHER PUBLICATIONS

Squitieri, F., & de Yebenes, J. G. (2015). Profile of pridopidine and its potential in the treatment of Huntington disease: the evidence to date. *Drug design, development and therapy*, 9, 5827.

Squitieri, F., et al. (2013). One-year safety and tolerability profile of pridopidine in patients with Huntington disease. *Neurology*, 80(12), 1086-1094.

Tedroff, J., et al. (1999). Long-lasting improvement following (−)-OSU6162 in a patient with Huntington's disease. *Neurology*, 53(7), 1605-1605.

Rabinovich-Guilatt et al. (2016)—The effect of mild and moderate renal impairment on the pharmacokinetics of pridopidine, a new drug for Huntington's disease—British journal of clinical pharmacology, 81(2), 246-255.

Cognition—Definition of Cognition by Oxford Online Dictionary. Oxford Univ Press https://www.oed.com/, Accessed Nov. 1989.

De Tommaso, Marina, et al. Effects of rivastigmine on motor and cognitive impairment in Huntington's disease. *Movement disorders*, 2004, 19.12: 1516-1518.

European Search Report for EP21153340.1 dated Jun. 24, 2021.

Grachev, Igor D., et al. Sigma-1 and dopamine D2/D3 receptor occupancy of pridopidine in healthy volunteers and patients with Huntington disease: a [18 F] fluspidine and [18 F] fallypride PET study. *European journal of nuclear medicine and molecular imaging*, 2021, 48.4: 1103-1115.

Jacqmin-Gadda, Helene, et al. A 5-year longitudinal study of the Mini-Mental State Examination in normal aging. *American journal of epidemiology*, 1997, 145.6: 498-506.

Johnston, Tom H., et al. Pridopidine, a clinic-ready compound, reduces 3,4-dihydroxyphenylalanine-induced dyskinesia in Parkinsonian macaques. *Movement Disorders*, 2019, 34.5: 708-716.

Kalueff, Allan V.; Tuohimaa, Pentti. Mouse grooming microstructure is a reliable anxiety marker bidirectionally sensitive to GABAergic drugs. European journal of pharmacology, 2005, 508.1-3: 147-153.

Mason, Sarah L., et al. Cognitive follow up of a small cohort of Huntington's disease patients over a 5 year period. PLoS currents, 2010, 2.

Nasreddine, Ziad S., et al. The Montreal Cognitive Assessment, MoCA: a brief screening tool for mild cognitive impairment. Journal of the Americen Geriatrics Society, 2005, 53.4: 695-699.

Reading, Paul J.; Luce, Anna K.; McKeith, Ian G. Rivastigmine in the treatment of parkinsonian psychosis and cognitve impairment: preliminary findings from an open trial. Movement disorders: official journal of the Movement Disorder Society, 2001, 16.6: 1171-1174.

Rösler, Michael, et al. Efficacy and safety of rivastigmine in patients with Alzheimer's disease: international randomised controlled trial Commentary: Another piece of the Alzheimer's jigsaw. Bmj, 1999, 318.7184: 633-640.

Sahlholm, Kristoffer, et al. Pridopidine selectively occupies sigma-1 rather than dopamine D2 receptors at behaviorally active doses. Psychopharmacology, 2015, 232.18: 3443-3453.

Seibenhener, Michael L.; Wooten, Michael C. Use of the open field maze to measure locomotor and anxiety-like behavior in mice. JoVE (oural of Visualized Experiments), 2015, 96: e52434.

Stout, Julie C., et al. HD-CAB: A cognitive assessment battery for clinical trials in Huntington's disease1, 2, 3. Movement Disorders, 2014, 29.10: 1281-1288.

Trung, Jessica, et al. Transcranial magnetic stimulation improves cognition over time in Parkinson's disease. Parkinsonism & related disorders, 2019, 66: 3-8.

Agosta, F. et al. (2012). Resting state fMRI in Alzheimer's disease: beyond the default mode network. *Neurobiology of Aging*, 33(8), 1564-1578.

Ates-Alagoz, Z. et al. (2013). NMDA receptor antagonists for treatment of depression. *Pharmaceuticals*, 6(4), 480-499.

Austin, M. P et al. (2001). Cognitive deficits in depression: possible implications for functional neuropathology. *The British Journal of Psychiatry*, 178(3), 200-206.

Balthazar, M et al. (2014). Alzheimer's s A Default Mode Network Disease: A Grey Matter, Functional, and Structural Connectivity Study. *Alzheimer's & Dementia*, 10, P391-P391.

Bonnelle, V. et al. (2012). Salience network integrity predicts default mode network function after traumatic brain injury. *Proceedings of the National Academy of Sciences*, 109(12), 4690-4695.

Bourne, J. N. et al. (2008). Balancing structure and function at hippocampal dendritic spines. *Annu. Rev. Neuroscience.*, 31, 47-67.

Brier, M. R. et al. (2014). Network dysfunction in Alzheimer's disease: refining the disconnection hypothesis. Brain connectivity, 4(5), 299-311.

Brito, V. et al. (2013). Imbalance of p75NTR/TrkB protein expression in Huntington's disease: implication for neuroprotective therapies. *Cell Death & Disease*, 4(4), e595-e595.

Bryan, K. J. et al. (2011). Transgenic mouse models of Alzheimer's disease: behavioral testing and considerations. Buccafusco JJ, editor. *Methods of Behavior Analysis in Neuroscience*. 2nd edition.

Buckner, R. L. et al. (2008). The brain's default network: anatomy, function, and relevance to disease. *Annals of the New York Academy of Sciences*. 1124(1), 1-38.

Callizot, N. et al. (2013). Operational dissection of p-amyloid cytopathic effects on cultured neurons. *Journal of Neuroscience Research*, 91(5), 706-716.

Combs, C. K. et al. (2000). Inflammatory mechanisms in Alzheimer's disease: inhibition of β-amyloid-stimulated proinflammatory responses and neurotoxicity by PPARy agonists. *Journal of Neuroscience*, 20(2), 558-567.

Coyle, J. T., & Tsai, G. (2004). NMDA receptor function, neuroplasticity, and the pathophysiology of schizophrenia. *International Review of Neurobiology*, 59, 491-515.

Cumming, T. B. et al. (2013). Stroke, cognitive deficits, and rehabilitation: still an incomplete picture. *International Journal of Stroke*, 8(1), 38-45.

Cummings, J. L. et al. (1998). Alzheimer's disease: etiologies, pathophysiology, cognitive reserve, and treatment opportunities. Neurology, 51(1 Suppl 1), S2-S17.

Detrait, E et al. (2010). Automation of continuous spontaneous alternation to increase the throughput for in vivo screening of cognitive enhancers. Optimization of the ethovision system for the Y-maze test in mice. *In Proceedings of Measuring Behavior* (pp. 141-144).

Dietz, D. M. et al. (2014). ΔFosB induction in prefrontal cortex by antipsychotic drugs is associated with negative behavioral outcomes. *Neuropsychopharmacology*, 39(3), 538-544.

Dubois, B. et al. (1997). Cognitive deficits in Parkinson's disease. *Journal of Neurology*, 244(1), 2-8.

Ferreri, F. et al. (2011). Current research on cognitive aspects of anxiety disorders. *Current Opinion in Psychiatry*, 24(1), 49-54.

Fioravanti, M. et al. (2012). Cognitive deficits in schizophrenia: an updated metanalysis of the scientific evidence. *BMC Psychiatry*, 12(1), 1-20.

Foroud, T. et al. (1995). Cognitive scores in carriers of Huntington's disease gene compared to noncarriers. Annals of Neurology: *Official Journal of the American Neurological Association and the Child Neurology Society*, 37(5), 657-664.

Francardo, V. et al. (2014). Pharmacological stimulation of sigma-1 receptors has neurorestorative effects in experimental parkinsonism. *Brain*, 137(7), 1998-2014.

Fujimoto, M. et al. (2012). Sigma-1 receptor chaperones regulate the secretion of brain-derived neurotrophic factor. *Synapse*, 66(7), 630-639.

Ghosh, B. C. et al. (2012). Social cognitive deficits and their neural correlates in progressive supranuclear palsy. *Brain*, 135(7), 2089-2102.

Girardi, A et al. (2011). Deficits in emotional and social cognition in amyotrophic lateral sclerosis. *Neuropsychology*, 25(1), 53.

Gould, T. J. (2010). Addiction and cognition. *Addiction Science & Clinical Practice*, 5(2), 4.

Graveland, G. A. et al. (1985). Evidence for degenerative and regenerative changes in neostriatal spiny neurons in Huntington's disease. *Science*, 227(4688), 770-773.

(56) References Cited

OTHER PUBLICATIONS

Guye, M. et al. (2010). Graph theoretical analysis of structural and functional connectivity MRI in normal and pathological brain networks. *Magnetic Resonance Materials in Physics, Biology and Medicine*, 23(5), 409-421.

Hart, R. P. et al. (2003). Cognitive impairment in patients with chronic pain: the significance of stress. *Current Pain and Headache Reports*, 7(2), 116-126.

Hazim, A. I. et al. (2011). The effects on motor behaviour and short-term memory tasks in mice following an acute administration of Mitragyna speciosa alkaloid extract and mitragynine. *Journal of Medicinal Plants Research*, 5(24), 5810-5817.

Hironaka, N. et al. (2001). Memory-related acetylcholine efflux from rat prefrontal cortex and hippocampus: a microdialysis study. *Brain Research*, 901(1-2), 143-150.

Hyrskyluoto, A. et al. (2013). Sigma-1 receptor agonist PRE084 is protective against mutant huntingtin-induced cell degeneration: involvement of calpastatin and the NF-κB pathway. *Cell Death & Disease*, 4(5), e646-e646.

Ishikawa, M. et al. (2010). The role of sigma-1 receptors in the pathophysiology of neuropsychiatric diseases. *Journal of Receptor. Ligand Channel Research*, 3, 25-36.

Jonkers, N. et al. (2000). MK801 influences L-DOPA-induced dopamine release in intact and hemi-parkinson rats. *European Journal of Pharmacology*, 407(3), 281-291.

Kawahara, M. et al. (2000). Molecular mechanism of neurodegeneration induced by Alzheimer's β-amyloid protein: channel formation and disruption of calcium homeostasis. *Brain Research Bulletin*, 53(4), 389-397.

Keefe, R. S. et al. (2014). Cognitive effects of pharmacotherapy for major depressive disorder: a systematic review. The Journal of Clinical Psychiatry, 75(8), 3169.

Kipps, C. M. et al. (2006). Theory of mind in frontotemporal dementia. Social Neuroscience, 1(3-4), 235-244.

Krabbendam, L. et al. (2000). Tardive dyskinesia is associated with impaired retrieval from long-term memory: the Curacao Extrapyramidal Syndromes Study: IV. *Schizophrenia Research*, 42(1), 41-46.

Kreitzer, A. C. (2008). Striatal plasticity and basal ganglia circuit function. *Neuron*, 60(4), 543-554.

Lucas-Jimenez, O. et al. (2016). Altered functional connectivity in the default mode network is associated with cognitive impairment and brain anatomical changes in Parkinson's disease. *Parkinsonism & Related Disorders*, 33, 58-64.

Luszczki, J. J. et al. (2005). Pharmacological and behavioral characteristics of interactions between vigabatrin and conventional antiepileptic drugs in pentylenetetrazole-induced seizures in mice: an isobolographic analysis. *Neuropsychopharmacology*, 30(5), 958-973.

Maurice, T. et al. (1997). SA4503, a novel cognitive enhancer with 01 receptor agonist properties, facilitates NMDA receptor-dependent learning in mice. *European Journal of Pharmacology*, 328(1), 9-18.

McKahnn, G. (1984). Clinical diagnosis of Alzheimer's disease; Report of the NINCDS-ADRDA Work Group under the auspices of Department of Health and Human Services Task Force on Alzheimer's Disease. *Neurology*, 34, 939-944.

McKhann, G. M. et al. (2011). The diagnosis of dementia due to Alzheimer's disease: Recommendations from the National Institute on Aging-Alzheimer's Association workgroups on diagnostic guidelines for Alzheimer's disease. *Alzheimer's & Dementia*, 7(3), 263-269.

Mevel, K. et al. (2011). The default mode network in healthy aging and Alzheimer's disease. *International Journal of Alzheimer's Disease*, 2011.

Miki, Y. et al. (2014). Accumulation of the sigma-1 receptor is common to neuronal nuclear inclusions in various neurodegenerative diseases. *Neuropathology*, 34(2), 148-158.

Newcomer, J, W. et. al. (2001). NMDA receptor regulation of memory and behavior in humans. *Hippocampus*, 11(5), 529-542.

Onaolapo, O. J. et al. (2012). Elevated plus maze and Y-Maze behavioral effects of subchronic, oral low dose monosodium glutamate in swiss albino mice. J. Pharm. Biol. Sci, 3, 21 -27.

Parada-Turska, J. et al. (1990). Excitatory amino acid antagonists and memory: effect of drugs acting at N-methyl-D-aspartate receptors in learning and memory tasks. *Neuropharmacology*, 29(12), 1111-1116.

Parent, M. B. et al. (2004). Septohippocampal acetylcholine: involved in but not necessary for learning and memory?. *Learning & Memory*, 11(1), 9-20.

Park, H. et al. (2013). Neurotrophin regulation of neural circuit development and function. *Nature Reviews Neuroscience*, 14(1), 7-23.

Petrella, J. R. et al. (2011). Default mode network connectivity in stable vs progressive mild cognitive impairment. *Neurology*, 76(6), 511-517.

Pike, C. J. et al. (1991). In vitro aging of β-amyloid protein causes peptide aggregation and neurotoxicity. *Brain Research*, 563(1-2), 311-314.

Rapaport, M. H. (2009). Future drugs for the treatment of depression: the need to look beyond monoamine systems. *CNS Spectrums*, 14(S5), 14-16.

Sakono, M. et al. (2010). Amyloid oligomers: formation and toxicity of Aβ oligomers. *The FEBS Journal*, 277(6), 1348-1358.

Sambataro, F. et al. (2010). Age-related alterations in default mode network: impact on working memory performance. *Neurobiology of Aging*, 31(5), 839-852.

Saunders, J. A et al. (2012). NMDA antagonist MK801 recreates auditory electrophysiology disruption present in autism and other neurodevelopmental disorders. *Behavioural Brain Research*, 234(2), 233-237.

Selkoe, D. J. (2001). Alzheimer's disease: genes, proteins, and therapy. *Physiological Reviews*.

Seo, J. S. et al. (1997). Effect of MK-801 on the Prevention and Treatment of Tardive Dyskinesia. *Korean Journal of Biological Psychiatry*, 4(2), 246-250.—Abstract.

Sisodia, S. S. et al. (1990). Evidence that β-amyloid protein in Alzheimer's disease is not derived by normal processing. *Science*, 248(4954), 492-495.

Stafstrom, C. E. et al. (1997). Acute effects of MK801 on kainic acid-induced seizures in neonatal rats. *Epilepsy Research*, 26(2), 335-344.

Stone, M. et al. (1998). Working and strategic memory deficits in schizophrenia. *Neuropsychology*, 12(2), 278.

Tsai, S. Y. et al. (2009). Sigma-1 receptors regulate hippocampal dendritic spine formation via a free radical-sensitive mechanism involving Rac1 GTP pathway. *Proceedings of the National Academy of Sciences*, 106(52), 22468-22473.

Van Den Buuse, M. et al. (2005). Importance of animal models in schizophrenia research. *Australian & New Zealand Journal of Psychiatry*,39(7), 550-557.

Van Rijckevorsel, K. (2006). Cognitive problems related to epilepsy syndromes, especially malignant epilepsies. *Seizure*, 15(4), 227-234.

Weinberger, D. R. et al. (1997). Cognitive function in schizophrenia. *International Clinical Psychopharmacology*.

Winkler, J. et al. (1995). Essential role of neocortical acetylcholine in spatial memory. *Nature*, 375(6531), 484-487.

Xie, Y. et al. (2010). BDNF overexpression in the forebrain rescues Huntington's disease phenotypes in YAC128 mice. *Journal of Neuroscience*, 30(44), 14708-14718.

Yagasaki, Y. et al. (2006). Chronic antidepressants potentiate via sigma-1 receptors the brain-derived neurotrophic factor-induced signaling for glutamate release. *Journal of Biological Chemistry*, 281(18), 12941-12949.

Zhou, J. et al. (2010). Divergent network connectivity changes in behavioural variant frontotemporal dementia and Alzheimer's disease. *Brain*, 133(5), 1352-1367.

\* cited by examiner

Hippocampal spines PS-KI mice

Hippocampal culture at DIV16. 16 h incubation with Pridopidine

USE OF PRIDOPIDINE TO IMPROVE COGNITIVE FUNCTION AND FOR TREATING ALZHEIMER'S DISEASE

CROSS REFERENCE TO RELATED APPLICATIONS

This application is a continuation-in-part application of U.S. patent application Ser. No. 15/052,368 filed Feb. 24, 2016, which claims the benefit of U.S. Provisional Application No. 62/186,221, filed Jun. 29, 2015, and U.S. Provisional Application No. 62/120,771, filed Feb. 25, 2015, the entire contents of which are hereby incorporated by reference herein.

Throughout this application, various publications are referred to by first author and year of publication. Full citations for these publications are presented in a References section immediately before the claims. Disclosures of the publications cited in the References section are hereby incorporated by reference in their entireties into this application in order to more fully describe the state of the art as of the date of the invention described herein.

BACKGROUND

Pridopidine (4-[3-(methylsulfonyl)phenyl]-1-propyl-piperidine, ACR16, Huntexil) is a drug under development from a new class of pharmaceutical agents, the dopidines, which are considered to have dopaminergic stabilizing properties (U.S. Patent Publication No. US 2014/0378508). Dopaminergic stabilizers are compounds that can both enhance and counteract dopamine dependent functions in the central nervous system (CNS), depending on the initial level of dopaminergic activity (U.S. Patent Publication No. US 2014/0378508). Dopaminergic stabilizers suppress the hyperactive behavior induced by stimulants such as amphetamine. In contrast, at low levels of dopamine function, the dopamine stabilizers enhance behavioral activity (U.S. Patent Publication No. US 2014/0378508). The primary effect of pridopidine on HD-related motor symptoms is therefore expected to occur via the dopamine transmissions modulating properties of pridopidine (Ponten 2010). Processes of synthesis of pridopidine and a pharmaceutically acceptable salt thereof are disclosed in U.S. Pat. No. 7,923,459. U.S. Pat. No. 6,903,120 claims pridopidine for the treatment of Parkinson's disease, dyskinesias, dystonias, Tourette's disease, iatrogenic and non-iatrogenic psychoses and hallucinoses, mood and anxiety disorders, sleep disorder, autism spectrum disorder, ADHD, Huntington's disease, age-related cognitive impairment, and disorders related to alcohol abuse and narcotic substance abuse.

Alzheimer's Disease

Alzheimer's disease (AD) is the most common form of dementia, a general term for memory loss and other intellectual abilities serious enough to interfere with daily life. AD accounts for 60 to 80 percent of dementia cases (www.alz.org).

AD is characterized by the loss of synapses and neurons from the brain, and by the accumulation of extracellular protein-containing deposits (referred to as 'senile plaques') and neurofibrillary tangles (Selkoe et al. 2001)

The most common early symptom of AD is difficulty remembering newly learned information. As AD advances it leads to increasingly severe symptoms, including disorientation, mood and behavior changes, as well as difficulty speaking, swallowing and walking.

Currently, there is no cure for AD. New effective therapies for AD are needed.

DMN (Default Mode Network)

The default mode network (DMN), is a large-scale brain network of interacting brain regions known to have activity highly correlated with each other and distinct from other networks in the brain. The DMN includes brain regions with high degrees of functional connectivity and is active in the brain at rest but becomes deactivated when task performance is initiated. The clinical implications of the DMN in neurological and neuropsychiatric disorders have been, and continue to be, targets of investigation. In disorders including AD, PD, TLE, ADHD, and mood disorders, the DMN has been implicated in neurobiological/neurocognitive pathophysiological models. (YALE JOURNAL OF BIOLOGY AND MEDICINE 89 (2016), pp. 49-57).

DMN (Default Mode Network) plays crucial role in cognitive processing, and dysfunction in the DMN is associated with aberrant behaviors and cognition in various NDDs (F. Sambataro et al, 2010; F. Agosta et al, 2012; Bonnelle V et al, 2012). The DMN is comprised of brain regions known to be involved in cognitive functions: posterior cingulate cortex (PCC), lateral parietal cortex and medial prefrontal cortex (mPFC), and prominent connections to nodes in the medial temporal lobe (MTL) and angular gyrus (Mevel K. et al, 2011; Buckner R. L. et al, 2008).

Specifically, aberrant DMN connectivity seems to be the most affected network in Dementia due to AD (Balthazar et al, AAN 2014). In AD, the DMN consistently shows reduced connectivity, and has even been shown to predict disease severity and progression (Petrella J R, et al, 2011; Brier M R. et al, 2014).

Impaired DMN connectivity is also described in patients with FTD (Zhou J, et al, 2010; Kipps C M. and Hodges J R., 2006), ALS (Girardi A, et al, 2011), PSP (Ghosh B C, et al, 2012), PD (Lucas-Jimenez et al, 2016), as well as in several neuropsychiatric diseases (Buckner R L et al, 2008).

Additional number of studies identified DMN disturbances in schizophrenia, autism, hyperactivity disorder, epilepsy and multiple sclerosis (M. Guye et al, 2010).

SUMMARY OF THE INVENTION

This invention provides a method of improving cognitive function in a human subject comprising administering to the subject an amount of pridopidine or a pharmaceutically acceptable salt thereof wherein the cognitive function in need for improvement is associated with DMN dysfunction.

This invention provides a method of treating a human subject afflicted with a disease selected from Alzheimer's disease and mild cognitive impairment (MCI) comprising administering to the subject a pharmaceutical composition comprising an amount of pridopidine or a pharmaceutically acceptable salt thereof wherein said disease is associated with DMN dysfunction.

In one embodiment, pridopidine increases the DMN functional connectivity (increased activity). In another embodiment, the increase in functional connectivity is in the insula. In another embodiment, the increase in functional connectivity is in the parietal and temporal cortex. In another embodiment, the increase in functional connectivity is in the precuneus.

This invention provides a method of treating a human subject afflicted with epilepsy, comprising administering to the subject a pharmaceutical composition comprising an amount of pridopidine or a pharmaceutically acceptable salt thereof.

This invention provides a method of improving cognitive function in a subject comprising periodically administering to the subject an amount of pridopidine or a pharmaceutically acceptable salt thereof effective to improve a cognitive function in the subject.

The invention also provides a package comprising:
a) a pharmaceutical composition comprising an amount of pridopidine or a pharmaceutically acceptable salt thereof and a pharmaceutically acceptable carrier;
b) instructions for use of the pharmaceutical composition to treat a subject afflicted with a disease or disorder associated with a cognitive deficit.

The invention also provides a therapeutic package for dispensing to, or for use in dispensing to, a subject afflicted with a disease or disorder associated with a cognitive deficit, which comprises:
a) one or more unit doses, each such unit dose comprising an amount of pridopidine or a pharmaceutically acceptable salt thereof, wherein the amount of said pridopidine in said unit dose is effective, upon administration to said subject, to treat the subject, and
b) a finished pharmaceutical container therefor, said container containing said unit dose or unit doses, said container further containing or comprising labeling directing the use of said package in the treatment of said subject.

The invention also provides a pharmaceutical composition comprising an amount of pridopidine or a pharmaceutically acceptable salt thereof for use in treating a subject afflicted with a disease or disorder associated with a cognitive deficit.

The invention also provides a pharmaceutical composition in a unit dosage form, useful in treating a subject afflicted with a disease or disorder associated with a cognitive deficit, which comprises an amount of pridopidine or a pharmaceutically acceptable salt thereof, wherein the amount of said pridopidine in said composition is effective, upon administration to said subject of one or more of said unit dosage forms of said composition, to treat the subject.

The invention also provides a package comprising:
a) a pharmaceutical composition; and
b) instructions for use of the pharmaceutical composition to treat a subject afflicted with a disease or disorder associated with a cognitive deficit.

This invention also provides pridopidine or a pharmaceutically acceptable salt thereof for use in treating a disease or disorder associated with a cognitive deficit.

This invention also provides a use of pridopidine or a pharmaceutically acceptable salt thereof in the manufacture of a medicament for treating a disease or disorder associated with a cognitive deficit.

Additionally, the invention provides a method of treating a subject afflicted with Alzheimer's disease, comprising periodically administering to the subject a pharmaceutical composition comprising an amount of pridopidine or a pharmaceutically acceptable salt thereof effective to treat the subject.

The invention also provides pridopidine or a pharmaceutically acceptable salt thereof for use in treating a subject afflicted with Alzheimer's disease.

The invention also provides pridopidine or a pharmaceutically acceptable salt thereof for the manufacture of a medicament for use in treating a subject afflicted with Alzheimer's disease.

The invention also provides a pharmaceutical composition comprising an effective amount of pridopidine or a pharmaceutically acceptable salt thereof for treating Alzheimer's disease.

The invention also provides a pharmaceutical composition comprising pridopidine or a pharmaceutically acceptable salt thereof for use in treating a subject suffering from Alzheimer's disease.

The invention also provides a package comprising:
a) a pharmaceutical composition comprising an amount of pridopidine; and
b) instructions for use of the pharmaceutical composition to treat a subject afflicted with a Alzheimer's disease.

The invention also provides a therapeutic package for dispensing to, or for use in dispensing to, a subject afflicted with Alzheimer's disease, which comprises:
a) one or more unit doses, each such unit dose comprising an amount of pridopidine thereof, wherein the amount of said pridopidine in said unit dose is effective, upon administration to said subject, to treat the subject, and
b) a finished pharmaceutical container therefor, said container containing said unit dose or unit doses, said container further containing or comprising labeling directing the use of said package in the treatment of said subject.

The invention also provides a package comprising:
a) a first pharmaceutical composition comprising an amount of pridopidine and a pharmaceutically acceptable carrier;
b) a second pharmaceutical composition comprising an amount of a drug approved to treat Alzheimer's disease and a pharmaceutically acceptable carrier, and
c) instructions for use of the first and second pharmaceutical compositions together to treat a subject afflicted with a Alzheimer's disease.

The invention also provides a package comprising:
a) a first pharmaceutical composition comprising an amount of pridopidine and a pharmaceutically acceptable carrier;
b) a second pharmaceutical composition comprising an amount of one or more antidepressants, anxiolytics, or antipsychotic medications, and a pharmaceutically acceptable carrier; and
c) instructions for use of the first and second pharmaceutical compositions together to treat a subject afflicted with Alzheimer's disease.

The invention also provides a therapeutic package for dispensing to, or for use in dispensing to, a subject afflicted with Alzheimer's disease, which comprises:
a) one or more unit doses, each such unit dose comprising:
  i) an amount of pridopidine and
  ii) an amount of a drug approved to treat Alzheimer's disease wherein the respective amounts of said pridopidine and said drug approved to treat Alzheimer's disease in said unit dose are effective, upon concomitant administration to said subject, to treat the subject, and
b) a finished pharmaceutical container therefor, said container containing said unit dose or unit doses, said container further containing or comprising labeling directing the use of said package in the treatment of said subject.

The invention also provides a therapeutic package for dispensing to, or for use in dispensing to, a subject afflicted with Alzheimer's disease, which comprises:

a) one or more unit doses, each such unit dose comprising:
    i) an amount of pridopidine and
    ii) an amount of one or more antidepressants, anxiolytics, or antipsychotic medications
    wherein the respective amounts of said pridopidine and said one or more antidepressants, anxiolytics, or antipsychotic medications in said unit dose are effective, upon concomitant administration to said subject, to treat the subject, and
  b) a finished pharmaceutical container therefor, said container containing said unit dose or unit doses, said container further containing or comprising labeling directing the use of said package in the treatment of said subject.

DETAILED DESCRIPTION OF THE INVENTION

Figure 1A:
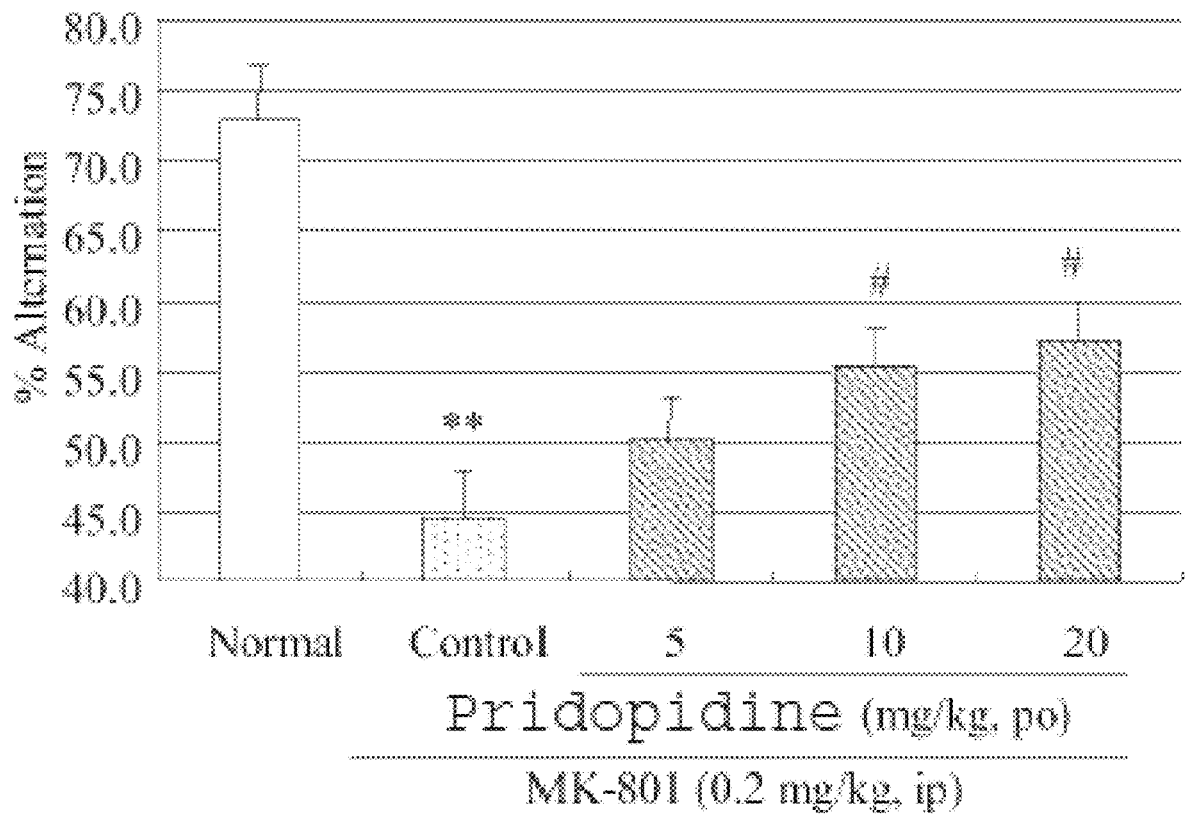
FIGS. 1A and 1B: Effect of pridopidine on the Disruption of Spontaneous Alternation (FIG. 1A) and the Increase in the Number of Total Arm Entries (FIG. 1B) Induced by MK-801 in a Y-maze. Data represents the mean±SEM. **$p<0.01$, statistically significant compared with the normal group (Student's t test). #$p<0.05$; statistically significant compared with the control group (Dunnett's multiple comparison test). Twelve mice were used in each group.

This invention provides a method of improving cognitive function in a subject comprising periodically administering to the subject an amount of pridopidine or a pharmaceutically acceptable salt thereof effective to improve a cognitive function in the subject.

This invention provides a method of improving cognitive function in a human subject comprising administering to the subject an amount of pridopidine or a pharmaceutically acceptable salt thereof wherein the cognitive function in need for improvement is associated with DMN dysfunction.

In an embodiment, the cognitive function is selected from the group consisting of global cognitive functioning, sustained cognition, memory, language, executive functioning, and attention. In another embodiment, the cognitive function is memory.

In an embodiment, memory is short term memory. In another embodiment, memory is long term memory. In another embodiment, memory is working memory.

In an embodiment, the subject is afflicted with a cognitive deficit. In another embodiment, the subject is prone to or predisposed to have a cognitive deficit.

In an embodiment, the cognitive deficit is a memory deficit.

In an embodiment, the memory deficit is a short-term memory deficit. In another embodiment, the memory deficit is memory loss.

In an embodiment, the memory loss is caused by one or more of age-related changes in memory, mild cognitive impairment, dementia or depression.

In an embodiment, the cognitive deficit is caused by or associated with a disease or disorder.

In an embodiment, the disease or disorder is a disease or disorder associated with NMDA receptor. In another embodiment, the disease or disorder is schizophrenia or autism. In another embodiment, the disease or disorder is epilepsy or an anxiety disorder. In another embodiment, the disease or disorder is amyotrophic lateral sclerosis (ALS). In another embodiment, the disease or disorder is frontotemporal dementia (FTD). In another embodiment, the disease or disorder is mild cognitive impairment (MCI). In another embodiment, the disease or disorder is bipolar disorder. In another embodiment, the disease or disorder is Huntington's disease. In another embodiment, the disease or disorder is selected from the group consisting of major depressive disorder (MDD), Parkinson's disease, Alzheimer's disease, tardive dyskinesia, depression, sickle cell anemia, stroke, chronic pain syndrome, and addiction. In another embodiment, the disease or disorder is selected from the group consisting of mild cognitive impairment, memory loss, memory deficit, a memory deficit related to brain injury or a post-stroke event, a learning deficiency, and behavioral and cognitive problems associated with brain tumors. In another embodiment, the disease or disorder is selected from the group consisting of dementia, dementia associated with Lewy Bodies, age-related cognitive decline, psychosis, attention deficit disorder (ADHD), bipolar disorder, brain injury, mood and affective disorders, Tourette's syndrome, mental retardation, progressive supranuclear palsy, Creutzfeldt-Jacob disease, corticobasal Degeneration, vascular dementia, and Pick's disease. In another embodiment, the disease or disorder is selected from the group consisting of generalized anxiety disorder (GAD), social anxiety disorder (SAD), tardive dyskinesia, depression, sickle cell anemia, chronic pain syndrome, addiction, nicotine addiction, internet addiction, cocaine addiction, tourette's syndrome, mental retardation, corticobasal degeneration, vascular dementia, pick's disease, posttraumatic stress disorder (PTSD), obsessive compulsive disorder, panic disorder (PD), trigeminal pain, trigeminal musculoskeletal pain, phantom limb pain, irritable bowel syndrome, blepharospasm, complex regional pain syndrome, chronic low back pain, autism spectrum disorder (ASD), infantile spasm (IS).

In one embodiment, this invention provides a method of treating a disease or disorder associated with DMN dysfunction comprising administering a pharmaceutical composition comprising pridopidine or any acceptable salt thereof.

In an embodiment, the amount of pridopidine or a pharmaceutically acceptable salt thereof is administered to the human subject once daily. In one embodiment, the amount of pridopidine or a pharmaceutically acceptable salt thereof is administered more often than once daily. In another embodiment, the amount of pridopidine or a pharmaceutically acceptable salt thereof is administered 2-4 times a day. In one embodiment, the amount of pridopidine or a pharmaceutically acceptable salt thereof is administered less than once a day. In another embodiment, the amount of pridopidine or a pharmaceutically acceptable salt thereof is administered 2-4 times a week.

In an embodiment, the periodic administration continues for at least 3 days, more than 30 days, more than 42 days, 8 weeks or more, at least 12 weeks, at least 24 weeks, more than 24 weeks, or 6 months or more.

In an embodiment, the amount of pridopidine administered is 1 mg/day-315 mg/day, 22.5 mg/day-315 mg/day or 90 mg/day-315 mg/day.

In another embodiment, the amount of pridopidine administered is about 22.5 mg/day, about 45 mg/day, about 67.5 mg/day, about 90 mg/day, about 100 mg/day, about 112.5 mg/day, about 125 mg/day, about 135 mg/day, about 150 mg/day, about 180 mg/day, about 200 mg/day, about 250 mg/day, or about 315 mg/day.

In an embodiment, the amount of pridopidine is administered orally. In another embodiment, the amount of pridopidine is administered parenterally. In another embodiment, the amount of pridopidine is administered intravascularly. In another embodiment, the amount of pridopidine is administered paracancerally. In another embodiment, the amount of pridopidine is administered transmucosally. In another embodiment, the amount of pridopidine is administered transdermally. In another embodiment, the amount of pridopidine is administered intramuscularly. In another embodiment, the amount of pridopidine is administered untranasally. In another embodiment, the amount of pridopidine is administered intravenously. In another embodiment, the amount of pridopidine is administered intradermally. In another embodiment, the amount of pridopidine is administered subcutaneously. In another embodiment, the amount of pridopidine is administered sublingually. In another embodiment, the amount of pridopidine is administered intraperitoneally. In another embodiment, the amount of pridopidine is administered intraventricularly. In another embodiment, the amount of pridopidine is administered intracranially. In another embodiment, the amount of pridopidine is administered intravaginally. In another embodiment, the amount of pridopidine is administered by inhalation. In another embodiment, the amount of pridopidine is administered rectally. In another embodiment, the amount of pridopidine is administered intratumorally.

In an embodiment, the pharmaceutically acceptable salt of pridopidine is pridopidine hydrochloride. In another embodiment, the pharmaceutically acceptable salt of pridopidine is pridopidine hydrobromide. In another embodiment, the pharmaceutically acceptable salt of pridopidine is pridopidine nitrate. In another embodiment, the pharmaceutically acceptable salt of pridopidine is pridopidine perchlorate. In another embodiment, the pharmaceutically acceptable salt of pridopidine is pridopidine phosphate. In another embodiment, the pharmaceutically acceptable salt of pridopidine is pridopidine sulphate. In another embodiment, the pharmaceutically acceptable salt of pridopidine is pridopidine formate. In another embodiment, the pharmaceutically acceptable salt of pridopidine is pridopidine acetate. In another embodiment, the pharmaceutically acceptable salt of pridopidine is pridopidine aconate. In another embodiment, the pharmaceutically acceptable salt of pridopidine is pridopidine ascorbate. In another embodiment, the pharmaceutically acceptable salt of pridopidine is pridopidine benzenesulphonate. In another embodiment, the pharmaceutically acceptable salt of pridopidine is pridopidine benzoate. In another embodiment, the pharmaceutically acceptable salt of pridopidine is pridopidine cinnamate. In another embodiment, the pharmaceutically acceptable salt of pridopidine is pridopidine citrate. In another embodiment, the pharmaceutically acceptable salt of pridopidine is pridopidine embonate. In another embodiment, the pharmaceutically acceptable salt of pridopidine is pridopidine enantate. In another embodiment, the pharmaceutically acceptable salt of pridopidine is pridopidine fumarate. In another embodiment, the pharmaceutically acceptable salt of pridopidine is pridopidine glutamate. In another embodiment, the pharmaceutically acceptable salt of pridopidine is pridopidine glycolate. In another embodiment, the pharmaceutically acceptable salt of pridopidine is pridopidine lactate. In another embodiment, the pharmaceutically acceptable salt of pridopidine is pridopidine maleate. In another embodiment, the pharmaceutically acceptable salt of pridopidine is pridopidine malonate. In another embodiment, the pharmaceutically acceptable salt of pridopidine is pridopidine mandelate. In another embodiment, the pharmaceutically acceptable salt of pridopidine is pridopidine methanesulphonate. In another embodiment, the pharmaceutically acceptable salt of pridopidine is pridopidine naphthalene-2-sulphonate. In another embodiment, the pharmaceutically acceptable salt of pridopidine is pridopidine phthalate. In another embodiment, the pharmaceutically acceptable salt of pridopidine is pridopidine salicylate. In another embodiment, the pharmaceutically acceptable salt of pridopidine is pridopidine sorbate. In another embodiment, the pharmaceutically acceptable salt of pridopidine is pridopidine stearate. In another embodiment, the pharmaceutically acceptable salt of pridopidine is pridopidine succinate. In another embodiment, the pharmaceutically acceptable salt of pridopidine is pridopidine tartrate. In another embodiment, the pharmaceutically acceptable salt of pridopidine is pridopidine toluene-p-sulphonate.

In an embodiment, the subject is a human patient.

The invention also provides a package comprising:

a) a pharmaceutical composition comprising an amount of pridopidine or a pharmaceutically acceptable salt thereof and a pharmaceutically acceptable carrier;

b) instructions for use of the pharmaceutical composition to treat a subject afflicted with a disease or disorder associated with a cognitive deficit.

In an embodiment, the disease or disorder is a disease or disorder associated with NMDA receptor.

In an embodiment, the cognitive deficit is memory loss.

In an embodiment, the pharmaceutically acceptable salt of pridopidine is pridopidine hydrochloride.

In an embodiment, the amount of pridopidine in the pharmaceutical composition is 1 mg-315 mg, 22.5 mg-315 mg or 90 mg-315 mg. In another embodiment, the amount of pridopidine in the pharmaceutical composition is about 22.5 mg, about 45 mg, about 67.5, mg, about 90 mg, about 100 mg, about 112.5 mg, about 125 mg, about 135 mg, about 150 mg, about 180 mg, about 200 mg, about 250 mg, or about 315 mg.

The invention also provides a therapeutic package for dispensing to, or for use in dispensing to, a subject afflicted with a disease or disorder associated with a cognitive deficit, which comprises:

a) one or more unit doses, each such unit dose comprising an amount of pridopidine or a pharmaceutically acceptable salt thereof, wherein the amount of said pridopidine in said unit dose is effective, upon administration to said subject, to treat the subject, and b) a finished pharmaceutical container therefor, said container containing said unit dose or unit doses, said container further containing or comprising labeling directing the use of said package in the treatment of said subject.

In an embodiment, the disease or disorder is a disease or disorder associated with NMDA receptor.

The invention also provides a pharmaceutical composition comprising an amount of pridopidine or a pharmaceutically acceptable salt thereof for use in treating a subject afflicted with a disease or disorder associated with a cognitive deficit.

In an embodiment, the pharmaceutical composition is in a solid, a capsule or a tablet form.

In an embodiment, the cognitive deficit is memory loss.

In an embodiment, the pharmaceutically acceptable salt of pridopidine is pridopidine hydrochloride.

In an embodiment, the amount of pridopidine in the pharmaceutical composition is 1 mg-315 mg, 22.5 mg-315 mg or 90 mg-315 mg. In an another embodiment, the amount of pridopidine in the pharmaceutical composition is about 22.5 mg, about 45 mg, about 67.5, mg, about 90 mg, about 100 mg, about 112.5 mg, about 125 mg, about 135 mg, about 150 mg, about 180 mg, about 200 mg, about 250 mg, or about 315 mg.

The invention also provides a pharmaceutical composition in a unit dosage form, useful in treating a subject afflicted with a disease or disorder associated with a cognitive deficit, which comprises an amount of pridopidine or a pharmaceutically acceptable salt thereof, wherein the amount of said pridopidine in said composition is effective, upon administration to said subject of one or more of said unit dosage forms of said composition, to treat the subject.

In an embodiment, the disease or disorder is a disease or disorder associated with NMDA receptor.

The invention also provides a package comprising:

a) a pharmaceutical composition; and b) instructions for use of the pharmaceutical composition to treat a subject afflicted with a disease or disorder associated with a cognitive deficit.

This invention also provides pridopidine or a pharmaceutically acceptable salt thereof for use in treating a disease or disorder associated with a cognitive deficit.

This invention also provides a use of pridopidine or a pharmaceutically acceptable salt thereof in the manufacture of a medicament for treating a disease or disorder associated with a cognitive deficit.

For the foregoing and following embodiments, each embodiment disclosed herein is contemplated as being applicable to each of the other disclosed embodiments. For instance, the elements recited in the method embodiments can be used in the pharmaceutical composition, package, and use embodiments described herein and vice versa.

The invention further provides a method of treating a subject afflicted with a disease selected from Alzheimer's disease and mild cognitive impairment (MCI), comprising periodically administering to the subject a pharmaceutical composition comprising an amount of pridopidine or a pharmaceutically acceptable salt thereof effective to treat the subject.

The invention further provides a method of treating a subject afflicted with a disease selected from Alzheimer's disease and mild cognitive impairment (MCI), comprising periodically administering to the subject a pharmaceutical composition comprising an amount of pridopidine or a pharmaceutically acceptable salt thereof effective to treat the subject, wherein the disease is associated with DMN dysfunction.

In an embodiment, the amount of pridopidine is effective to reduce neurotoxicity in the subject. In another embodiment, the amount of pridopidine is effective to inhibit the progression Alzheimer's disease or MCI in the subject. In a further embodiment, the amount of pridopidine is effective to reduce one or more symptoms of Alzheimer's disease or MCI in the subject.

In an embodiment, the one or more symptoms are selected from the group consisting of cognitive impairment, function performance impairment, impairment in basic and instrumental activities of daily living, reduced quality of life and psychopathology.

In one embodiment, the one or more symptoms are measured by the Clinician's Interview-based Impression of Change plus Caregiver Input (CIBIC-Plus), Severity Impairment Battery (SIB), Alzheimer's Disease Cooperative Study Clinician's Global Impression of Change (ADCS-CCGIC), Alzheimer's Disease Assessment Scale-Cognitive (ADAS-Cog), Clinical Dementia Rating (CDR), CIBIC Plus-J Score Mental Function Impairment Scale (MENFIS), Mini-mental state exam (MMSE), Mini-cog test, Blessed Information-Memory-Concentration Test (BIMC), Cambridge Neuropsychological Test Automated Battery (CANTAB), Alzheimer's Disease Cooperative Study Activities of Daily Living Inventory (ADCS-ADL) Score, ADCS-ADL-SIV (severe impairment version), Disability Assessment for Dementia (DAD), the Functional Assessment Questionnaire (FAQ), Instrumental Activities of Daily Living (IADL), Physical Self-Maintenance Scale (PSMS) and Progressive Deterioration Scale (PDS), the Neuropsychiatric Inventory (NPI) score, CIBIC Plus-J Score Behavioral Pathology in Alzheimer's Disease Rating Scale (Behave-AD), CIBIC Plus-J Score Mental Function Impairment Scale (MENFIS), the Resource Utilization in Dementia-Lite (RUD-Lite), EuroQol 5-Dimensional Health-Related Quality of Life Scale (EQ-5D), the Clinical Global Impression of Change (CGIC), the Clinical Interview-Based Impression (CIBI), the Global Deterioration Scale (GDS), A Cognitive Assessment Battery for Clinical Trials in Huntington's Disease (HD-CAB), Montreal Cognitive Assessment (MoCA), Stroop Word Reading (SWR) or Symbol Digit Modalities Test (SDMT).

In an embodiment, the periodic administration is oral.

In an embodiment, between 1 mg-315 mg, 22.5-315 mg or 90 mg-315 mg pridopidine is administered to the patient per day. In another embodiment, about 22.5 mg, about 45 mg, about 67.5, mg, about 90 mg, about 100 mg, about 112.5 mg, about 125 mg, about 135 mg, about 150 mg, about 180 mg, about 200 mg, about 250 mg, or about 315 mg pridopidine is administered to the patient per day.

In an embodiment, the amount of pridopidine is administered by a unit dose of about 22.5 mg, about 45 mg, about 67.5, mg, about 90 mg, about 100 mg, about 112.5 mg, about 125 mg, about 135 mg, about 150 mg, about 180 mg, about 200 mg, about 250 mg, or about 315 mg pridopidine.

In an embodiment, the unit dose is administered once daily.

In an embodiment, the unit dose is administered more than once daily. In one embodiment, the unit dose is administered 2-4 times a day. In another embodiment, the unit dose is administered twice per day. In one embodiment, the unit dose is administered less than once a day. In one embodiment, the unit dose is administered 2-4 times per week.

In an embodiment, the pridopidine is in the form of pridopidine hydrochloride.

In an embodiment, the subject is a naïve subject.

In an embodiment, the method further comprises the administration of a drug approved to treat Alzheimer's disease or MCI. In another embodiment, the method further comprises the administration of a psychiatric drug. In an embodiment, the drug approved to treat Alzheimer's disease is donepezil, rivastigmine, galantamine, tacrine, or memantine.

In an embodiment, the method further comprises the administration of a psychiatric drug, an antidepressant drug, anxiolytics, antipsychotic medications or combinations thereof.

In an embodiment, the method further comprises the administration of one or more antidepressants. In another embodiment, the antidepressant is selected from the group consisting of citalopram, fluoxetine, paroxeine, sertraline, and trazodone.

In an embodiment, the method further comprises the administration of one or more anxiolytics. In another embodiment, the anxiolytic is selected from the group consisting of lorazepam and oxazepam.

In an embodiment, the method further comprises the administration of one or more antipsychotic medications. In another embodiment, the antipsychotic medication is selected from the group consisting of aripiprazole, clozapine, haloperidol, olanzapine, quetiapine, risperidone, and ziprasidone. The invention also provides pridopidine or a pharmaceutically acceptable salt thereof for use in treating a human subject afflicted with Alzheimer's disease.

The invention provides a method of treating a human subject afflicted with epilepsy, comprising administering to the subject a pharmaceutical composition comprising an amount of pridopidine or a pharmaceutically acceptable salt thereof.

In an embodiment, the amount of pridopidine or a pharmaceutically acceptable salt thereof is administered to the human subject once daily. In one embodiment, the amount of pridopidine or a pharmaceutically acceptable salt thereof is administered more often than once daily.

In an embodiment, the amount of pridopidine administered is 1 mg/day-315 mg/day, 22.5 mg/day-315 mg/day or 90 mg/day-315 mg/day.

In an embodiment, the amount of pridopidine is administered orally. In another embodiment, the amount of pridopidine is administered parenterally. In another embodiment, the amount of pridopidine is administered intravascularly. In another embodiment, the amount of pridopidine is administered paracancerally. In another embodiment, the amount of pridopidine is administered transmucosally. In another embodiment, the amount of pridopidine is administered transdermally. In another embodiment, the amount of pridopidine is administered intramuscularly. In another embodiment, the amount of pridopidine is administered untranasally. In another embodiment, the amount of pridopidine is administered intravenously. In another embodiment, the amount of pridopidine is administered intradermally. In another embodiment, the amount of pridopidine is administered subcutaneously. In another embodiment, the amount of pridopidine is administered sublingually. In another embodiment, the amount of pridopidine is administered intraperitoneally.

In another embodiment, the amount of pridopidine is administered intraventricularly. In another embodiment, the amount of pridopidine is administered intracranially. In another embodiment, the amount of pridopidine is administered intravaginally. In another embodiment, the amount of pridopidine is administered by inhalation. In another embodiment, the amount of pridopidine is administered rectally. In another embodiment, the amount of pridopidine is administered intratumorally.

In an embodiment, the pharmaceutically acceptable salt of pridopidine is pridopidine hydrochloride.

The invention also provides pridopidine or a pharmaceutically acceptable salt thereof for the manufacture of a medicament for use in treating a subject afflicted with Alzheimer's disease.

The invention also provides a pharmaceutical composition comprising an effective amount of pridopidine or a pharmaceutically acceptable salt thereof for treating Alzheimer's disease.

The invention also provides a pharmaceutical composition comprising pridopidine or a pharmaceutically acceptable salt thereof for use in treating a subject suffering from Alzheimer's disease.

The invention also provides a package comprising:
a) a pharmaceutical composition comprising an amount of pridopidine; and
b) instructions for use of the pharmaceutical composition to treat a subject afflicted with a Alzheimer's disease.

The invention also provides a therapeutic package for dispensing to, or for use in dispensing to, a subject afflicted with Alzheimer's disease, which comprises:
a) one or more unit doses, each such unit dose comprising an amount of pridopidine thereof, wherein the amount of said pridopidine in said unit dose is effective, upon administration to said subject, to treat the subject, and
b) a finished pharmaceutical container therefor, said container containing said unit dose or unit doses, said container further containing or comprising labeling directing the use of said package in the treatment of said subject.

The method of reducing neurotoxicity in a human patient afflicted with Alzheimer's disease, comprising periodically administering to the patient a pharmaceutical composition comprising pridopidine or a pharmaceutically acceptable salt thereof effective to treat the subject.

In an embodiment, the subject is a human subject.

The invention also provides a package comprising:
a) a first pharmaceutical composition comprising an amount of pridopidine and a pharmaceutically acceptable carrier;

b) a second pharmaceutical composition comprising an amount of a drug approved to treat Alzheimer's disease and a pharmaceutically acceptable carrier, and c) instructions for use of the first and second pharmaceutical compositions together to treat a subject afflicted with a Alzheimer's disease.

In an embodiment, the drug approved to treat Alzheimer's disease is donepezil, rivastigmine, galantamine, tacrine, or memantine.

The invention also provides a package comprising:

a) a first pharmaceutical composition comprising an amount of pridopidine and a pharmaceutically acceptable carrier;

b) a second pharmaceutical composition comprising an amount of one or more antidepressants, anxiolytics, or antipsychotic medications, and a pharmaceutically acceptable carrier; and c) instructions for use of the first and second pharmaceutical compositions together to treat a subject afflicted with Alzheimer's disease.

In an embodiment, the antidepressant is selected from the group consisting of citalopram, fluoxetine, paroxeine, sertraline, and trazodone.

In an embodiment, the anxiolytic is selected from the group consisting of lorazepam and oxazepam.

In an embodiment, the antipsychotic medication is selected from the group consisting of aripiprazole, clozapine, haloperidol, olanzapine, quetiapine, risperidone, and ziprasidone.

The invention also provides a therapeutic package for dispensing to, or for use in dispensing to, a subject afflicted with Alzheimer's disease, which comprises:

a) one or more unit doses, each such unit dose comprising:
i) an amount of pridopidine and
ii) an amount of a drug approved to treat Alzheimer's disease
wherein the respective amounts of said pridopidine and said drug approved to treat Alzheimer's disease in said unit dose are effective, upon concomitant administration to said subject, to treat the subject, and b) a finished pharmaceutical container therefor, said container containing said unit dose or unit doses, said container further containing or comprising labeling directing the use of said package in the treatment of said subject.

In an embodiment, the drug approved to treat Alzheimer's disease is donepezil, rivastigmine, galantamine, tacrine, or memantine.

The invention also provides a therapeutic package for dispensing to, or for use in dispensing to, a subject afflicted with Alzheimer's disease, which comprises:

a) one or more unit doses, each such unit dose comprising:
i) an amount of pridopidine and
ii) an amount of one or more antidepressants, anxiolytics, or antipsychotic medications
wherein the respective amounts of said pridopidine and said one or more antidepressants, anxiolytics, or antipsychotic medications in said unit dose are effective, upon concomitant administration to said subject, to treat the subject, and b) a finished pharmaceutical container therefor, said container containing said unit dose or unit doses, said container further containing or comprising labeling directing the use of said package in the treatment of said subject.

In an embodiment, the antidepressant is selected from the group consisting of citalopram, fluoxetine, paroxeine, sertraline, and trazodone.

In an embodiment, the anxiolytic is selected from the group consisting of lorazepam and oxazepam.

In an embodiment, the antipsychotic medication is selected from the group consisting of aripiprazole, clozapine, haloperidol, olanzapine, quetiapine, risperidone, and ziprasidone.

Combinations of the above-described embodiments are also within the scope of the invention.

The antipsychotic medication may be used to treat hallucinations, delusions, aggression, agitation, hostility and/or uncooperativeness. The anxiolytic may be used to treat anxiety, restlessness, verbally disruptive behavior and/or resistance. The antidepressant may be used to treat low mood and irritability (www.alz.org).

For the foregoing embodiments, each embodiment disclosed herein is contemplated as being applicable to each of the other disclosed embodiments. In addition, the elements recited in pharmaceutical composition embodiments can be used in the method and use embodiments described herein.

Terms

As used herein, and unless stated otherwise, each of the following terms shall have the definition set forth below.

As used herein, "administering to the subject" means the giving of, dispensing of, or application of medicines, drugs, or remedies to a subject to relieve, cure or reduce the symptoms associated with a disease, disorder or condition, e.g., a pathological condition. Oral administration is one way of administering the instant compounds to the subject.

As used herein, "cognitive function" means an intellectual process by which one becomes aware of, perceives, or comprehends ideas. Cognitive function involves all aspects of perception, thinking, reasoning, and memory, including short term memory.

As used herein, "improving cognitive function" includes slowing, stopping, or reversing the progression of a cognitive deficit, in addition to increasing cognitive function. Areas of cognitive function are described in Fioravanti et al (2012).

As used herein, a "cognitive deficit" is an inclusive term to describe any characteristic that acts as a barrier to cognitive function. Cognitive deficits can include loss of higher reasoning, forgetfulness, learning disabilities, concentration difficulties, decreased intelligence, and other reductions in mental functions. Cognitive deficits may be congenital or caused by environmental factors, brain injuries, neurological disorders, or mental illness. Cognitive impairments and cognitive dysfunctions are also considered cognitive deficits.

As used herein, "short term memory" is the capacity to recognize, recall and regurgitate small amounts of information shortly after its occurrence.

MK-801, or Dizocilpine, is an NMDA receptor antagonist.

As used herein, a "disease or disorder associated with an NMDA receptor" is any disease or disorder related to or resulting from NMDA receptor imbalance or dysfunction. This can include, but is not limited to, diseases or disease symptoms that can be induced or caused by NMDA receptor antagonists such as MK-801, diseases which may be treated by NMDA receptor antagonists such as MK-801, or diseases in which NMDA receptor antagonists such as MK-801 increase or decrease the severity of the symptoms.

The methods of the present invention are useful for improving cognitive function in diseases and disorders associated with both cognitive deficits and the NMDA receptor. The following diseases and disorders are associated with cognitive deficits and the NMDA receptor: schizophrenia, autism (Saunders, 2012), epilepsy (van Rijckevorsel 2006, Stafstrom 1997), anxiety disorders (Ferreri 2011, Dietz 2014), major depressive disorder (MDD) (Keefe 2014, Rapaport 2009), Parkinson's disease (Dubois 1997, Jonkers 2000), Alzheimer's disease (U.S. Patent Publication No. 20130065966), tardive dyskinesia (Krabbendam 2000, Seo 1997), Depression (Austin 2001, Ates-Alagoz 2013), sickle cell anemia (Steen 2005, U.S. Pat. No. 8,680,042), stroke (Cumming 2013, U.S. Patent Publication No. 20130065966), chronic pain syndrome (Hart 2003, Zeynep 2013), addiction (Gould 2010, U.S. Pat. No. 5,321,012), and Huntington's disease (Foroud 1995, U.S. Patent Publication No. 20130065966).

Other diseases and disorders which may be treated by the methods of this invention include: memory deficit, mild cognitive impairment, memory loss, a memory deficit related to brain injury or a post-stroke event, a learning deficiency, and behavioral and cognitive problems associated with brain tumors.

Additional diseases and disorders which may be treated by the methods of this invention include: dementia, dementia associated with Lewy Bodies, age-related cognitive decline, psychosis, attention deficit disorder (ADHD), bipolar disorder, brain injury, mood and affective disorders, Tourette's syndrome, mental retardation, progressive supranuclear palsy, Creutzfeldt-Jacob disease, vascular dementia, Corticobasal Degeneration, Creutzfeldt-Jakob Disease, and Pick's disease.

As used herein, an "amount" or "dose" of pridopidine as measured in milligrams refers to the milligrams of pridopidine (4-[3-(methylsulfonyl)phenyl]-1-propyl-piperidine) present in a preparation, regardless of the form of the preparation. For example, a unit dose containing "90 mg pridopidine" means the amount of pridopidine base in a preparation is 90 mg, regardless of the form of the preparation. Thus, when in the form of a salt, e.g. pridopidine hydrochloride salt, the weight of the salt form necessary to provide a dose of 90 mg pridopidine would be greater than 90 mg due to the presence of the salt.

As used herein, a "unit dose", "unit doses" and "unit dosage form(s)" mean a single drug administration entity/entities.

As used herein, "about" in the context of a numerical value or range means ±10% of the numerical value or range recited or claimed.

As used herein, "effective" as in an amount effective to achieve an end means the quantity of a component that is sufficient to yield an indicated therapeutic response without undue adverse side effects (such as toxicity, irritation, or allergic response) commensurate with a reasonable benefit/risk ratio when used in the manner of this disclosure. For example, an amount effective to treat cognitive deficit. The specific effective amount varies with such factors as the particular condition being treated, the physical condition of the patient, the type of mammal being treated, the duration of the treatment, the nature of concurrent therapy (if any), and the specific formulations employed and the structure of the compounds or its derivatives.

As used herein, to "treat" or "treating" encompasses, e.g., inducing inhibition, regression, or stasis of a disorder and/or disease, e.g. AD, or alleviating, lessening, suppressing, inhibiting, reducing the severity of, eliminating or substantially eliminating, or ameliorating a symptom of the disease or disorder.

As used herein, "inhibition" of disease progression or disease complication in a subject means preventing, delaying or reducing the disease progression and/or disease complication in the subject. This includes, for example, delaying the progression of one of more symptoms in the subject, including for example delaying the progression of cognitive impairment, delaying the deterioration in function performance and basic and instrumental activities of daily living, delaying the deterioration of quality of life or delaying the deterioration of psychopathology.

A "symptom" associated with AD includes any clinical or laboratory manifestation associated with AD and is not limited to what the subject can feel or observe. Symptoms of AD include but are not limited to the impairment and/or deterioration in cognition (e.g., memory and behavior, judgment/problem solving, attention, concentration, naming, comprehension, reasoning, language, communication, orientation and praxis), functional performance (e.g., grooming, dressing, walking including balance, bathing, feeding and toileting) basic and instrumental activities of daily living (e.g., shopping, preparing meals, using household appliances, conducting hobbies and interests, keeping appointments and reading), quality of life (e.g., mobility, self-care, daily activities, pain/discomfort, mood, relationships, overall physical condition, anxiety and depression, swallowing), or psychopathology (e.g. paranoid and delusional ideation, hallucinations, activity disturbances, diurnal rhythm disturbances, aggressiveness, affective disorders and anxieties, and phobias).

Various assessment tools are accepted in the field, which serve to evaluate the status of AD patients. For example, Cognition may be evaluated by various assessment tools exemplified by the Clinician Interview-Based Impression of Change, plus career interview (CIBIC-Plus), Severity Impairment Battery (SIB), Alzheimer's Disease Cooperative Study Clinician's Global Impression of Change (ADCS-CCGIC), Alzheimer's Disease Assessment Scale-Cognitive (ADAS-Cog), Clinical Dementia Rating (CDR), CIBIC Plus-J Score Mental Function Impairment Scale (MENFIS), Mini-mental state exam (MMSE), Mini-cog test, Blessed Information-Memory-Concentration Test (BIMC), and Cambridge Neuropsychological Test Automated Battery (CANTAB). Functional performance and basic and instrumental activities of daily living can be evaluated for example using Alzheimer's Disease Cooperative Study Activities of Daily Living Inventory (ADCS-ADL) Score, ADCS-ADL-SIV (severe impairment version), Disability Assessment for Dementia (DAD), Functional Assessment Questionnaire (FAQ), Instrumental Activities of Daily Living (IADL), Physical Self-Maintenance Scale (PSMS) and Progressive Deterioration Scale (PDS). Psychopathology can be evaluated for example by Neuropsychiatric Inventory (NPI) score, CIBIC Plus-J Score Behavioral Pathology in Alzheimer's Disease Rating Scale (Behave-AD), CIBIC Plus-J Score Mental Function Impairment Scale (MENFIS). Quality of life can be evaluated for example by the Resource Utilization in Dementia-Lite (RUD-Lite), EuroQol 5-Dimensional Health-Related Quality of Life Scale (EQ-SD), including for example Proxy Version (EQ-SD Proxy). In addition, global assessment measures may be used to evaluate the patient's status, indulging for example Clinical Global Impression of Change (CGIC), Clinical Interview-Based Impression (CIBI), Global Deterioration Scale (GDS).

A "biomarker" is a measurable parameter that serves as an indication to the severity, subtype or stage of the disease. Biomarkers for AD include but are not limited to Amyloid Beta (Aβ) 1-42 plasma concentration, change in glucose metabolism in the brain measured for example by Positron Emission Tomography (PET), and change in hyppocampal volume, measured for example by Magnetic Resonance Imaging (MRI). An increased Amyloid Beta (Aβ) 1-42 plasma concentration, reduced glucose metabolism in the brain, and reduced hyppocampal volume are considered to be associated with increased severity of the disease.

As used herein, "a subject afflicted with AD" means a subject diagnosed as suffering from AD, including for example subjects diagnosed as suffering from "definite AD", "probable AD" or "possible AD". In an embodiment, the subject is diagnosed as according to the 1984 Criteria, also called the NINCDS-ADRDA Alzheimer's criteria (McKhann et al. 1984). In another embodiment, the subject is diagnosed according to the revised criteria for diagnosis of Alzheimer's disease of the National Institute on Aging-Alzheimer's Association diagnostic guidelines for Alzheimer's disease (McKhann et al. 2011). In another embodiment, the subject is diagnosed according to the DSM-IV criteria. In another embodiment, the subject is diagnosed according to the International Classification of Diseases.

"Adverse event" or "AE" means any untoward medical occurrence in a clinical trial subject administered a medicinal product and which does not have a causal relationship with the treatment. An adverse event can therefore be any unfavorable and unintended sign including an abnormal laboratory finding, symptom, or diseases temporally associated with the use of an investigational medicinal product, whether or not considered related to the investigational medicinal product.

As used herein, a subject at "baseline" is a subject prior to initiating periodic administration of pridopidine.

As used herein, a "naïve subject" or a "naïve patient" with respect to a drug or therapy means that the subject has not previously received the drug or therapy.

A "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

As used herein, the term "pridopidine" refers to pridopidine free base. In certain embodiments, pridopidine also includes any pharmaceutically acceptable salt, such as the HCl salt or tartrate salt. Preferably, in any embodiments of the invention as described herein, the pridopidine is in the form of its hydrochloride salt.

As used herein, "combination" means an assemblage of reagents for use in therapy either by simultaneous or contemporaneous administration. Simultaneous administration refers to administration of an admixture (whether a true mixture, a suspension, an emulsion or other physical combination) of the pridopidine and the second compound. In this case, the combination may be the admixture or separate containers of the pridopidine and the second compound that are combined just prior to administration. Contemporaneous administration refers to the separate administration of the pridopidine and the second compound at the same time, or at times sufficiently close together that an additive or preferably synergistic activity relative to the activity of either the pridopidine and the second compound alone is observed.

As used herein, "concomitant administration" or administering "concomitantly" means the administration of two agents given in close enough temporal proximately to allow the individual therapeutic effects of each agent to overlap.

As used herein, "add-on" or "add-on therapy" means an assemblage of reagents for use in therapy, wherein the subject receiving the therapy begins a first treatment regimen of one or more reagents prior to beginning a second treatment regimen of one or more different reagents in addition to the first treatment regimen, so that not all of the reagents used in the therapy are started at the same time. For example, adding pridopidine therapy to a patient already receiving donepezil therapy.

A dosage unit as used herein may comprise a single compound or mixtures of compounds thereof. A dosage unit can be prepared for oral dosage forms, such as tablets, capsules, pills, powders, and granules.

Pharmaceutically Acceptable Salts

The active compounds for use according to the invention may be provided in any form suitable for the intended administration. Suitable forms include pharmaceutically (i.e. physiologically) acceptable salts, and pre- or prodrug forms of the compound of the invention.

In an embodiment, the pharmaceutically acceptable salt of pridopidine is pridopidine hydrochloride. In another embodiment, the pharmaceutically acceptable salt of pridopidine is pridopidine hydrobromide. In another embodiment, the pharmaceutically acceptable salt of pridopidine is pridopidine nitrate. In another embodiment, the pharmaceutically acceptable salt of pridopidine is pridopidine perchlorate. In another embodiment, the pharmaceutically acceptable salt of pridopidine is pridopidine phosphate. In another embodiment, the pharmaceutically acceptable salt of pridopidine is pridopidine sulphate. In another embodiment, the pharmaceutically acceptable salt of pridopidine is pridopidine formate. In another embodiment, the pharmaceutically acceptable salt of pridopidine is pridopidine acetate. In another embodiment, the pharmaceutically acceptable salt of pridopidine is pridopidine aconate. In another embodiment, the pharmaceutically acceptable salt of pridopidine is pridopidine ascorbate. In another embodiment, the pharmaceutically acceptable salt of pridopidine is pridopidine benzenesulphonate. In another embodiment, the pharmaceutically acceptable salt of pridopidine is pridopidine benzoate. In another embodiment, the pharmaceutically acceptable salt of pridopidine is pridopidine cinnamate. In another embodiment, the pharmaceutically acceptable salt of pridopidine is pridopidine citrate. In another embodiment, the pharmaceutically acceptable salt of pridopidine is pridopidine embonate. In another embodiment, the pharmaceutically acceptable salt of pridopidine is pridopidine enantate. In another embodiment, the pharmaceutically acceptable salt of pridopidine is pridopidine fumarate. In another embodiment, the pharmaceutically acceptable salt of pridopidine is pridopidine glutamate. In another embodiment, the pharmaceutically acceptable salt of pridopidine is pridopidine glycolate. In another embodiment, the pharmaceutically acceptable salt of pridopidine is pridopidine lactate. In another embodiment, the pharmaceutically acceptable salt of pridopidine is pridopidine maleate. In another embodiment, the pharmaceutically acceptable salt of pridopidine is pridopidine malonate. In another embodiment, the pharmaceutically acceptable salt of pridopidine is pridopidine mandelate. In another embodiment, the pharmaceutically acceptable salt of pridopidine is pridopidine methanesulphonate. In another embodiment, the pharmaceutically acceptable salt of pridopidine is pridopidine naphthalene-2-sulphonate. In another embodiment, the pharmaceutically acceptable salt of pridopidine is pridopidine phthalate. In another embodiment, the pharmaceutically acceptable salt of pridopidine is pridopidine salicylate. In another embodiment, the pharmaceutically acceptable salt of pridopidine is pridopidine sorbate. In another embodiment, the pharmaceutically acceptable salt of pridopidine is pridopidine stearate. In another embodiment, the pharmaceutically acceptable salt of pridopidine is pridopidine succinate. In another embodiment, the pharmaceutically acceptable salt of pridopidine is pridopidine tartrate. In another embodiment, the pharmaceutically acceptable salt of pridopidine is pridopidine toluene-p-sulphonate.

Such salts may be formed by procedures well known and described in the art.

Pharmaceutical Compositions

While the compounds for use according to the invention may be administered in the form of the raw compound, it is preferred to introduce the active ingredients, optionally in the form of physiologically acceptable salts, in a pharmaceutical composition together with one or more adjuvants, excipients, carriers, buffers, diluents, and/or other customary pharmaceutical auxiliaries.

In an embodiment, the invention provides pharmaceutical compositions comprising the active compounds or pharmaceutically acceptable salts or derivatives thereof, together with one or more pharmaceutically acceptable carriers therefore, and, optionally, other therapeutic and/or prophylactic ingredients know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by the skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

It is understood that where a parameter range is provided, all integers within that range, and tenths thereof, are also provided by the invention. For example, "0.1 mg-40.0 mg" includes 0.1 mg, 0.2 mg, 0.3 mg, 0.4 mg, etc. up to 40.0 mg.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1: Pridopidine Attenuates the MK-801-Induced Deficit of Working Memory in Y-Maze Mice This Example examines the effect of pridopidine on the deficits of working memory and the increase in total arm entries induced by MK-801 in the mouse Y-maze.

Materials and Methods

Animals: Male ddY mice (Japan SLC Inc., Shizuoka, Japan) aged 5 weeks were used. The mice were maintained with free access to laboratory chow and water. The mice were placed in the experiment room at least 1 h before the experiment.

Drugs: Pridopidine hydrochloride was dissolved in water and administered orally. (+)-MK-801 hydrogen maleate (dizocilpine hydrogen maleate) (commercially available from Sigma-Aldrich (St. Louis, Mo., USA)) was dissolved in saline and administered intraperitoneally. The drugs were administered at a volume of 10 mL/kg. The dose levels of pridopidine are presented as the amount of free base.

Y-maze: The Y-maze is a learning and memory test for rodents (van den Buuse 2005). Y-maze test is based on the innate curiosity of rodents to explore novel environments (Luszczki et al., 2005). It is used to assess exploratory behaviours, learning and memory function, short term memory, working memory, general locomotor activity, and stereotypic behavior in rodents (Hazim 2011, Onaolapo 2012, Detrait 2010).

Rodents exhibit a tendency to alternate between maze arms, thereby providing a measure of short term spatial memory. A high alternation rate is indicative of sustained cognition as the animals must remember which arm was entered last to not reenter it (Bryan 2009).

The Y-maze was made of gray vinyl chloride. Each arm was 40 cm long, 13 cm high, 3 cm wide at the bottom, and 10 cm wide at the top. All arms converged at equal angles.

Experimental Procedure: The present experiments were carried out according to the method established by Maurice et al. (1997). Pridopidine was administered, followed by MK-801 10 minutes later. Twenty minutes after administration of MK-801, each mouse was placed at the end of one arm and allowed to move freely through the maze during an 8-minute session. The series of arm entries were recorded. Alternation was defined as visits into all three arms on consecutive occasions. The number of maximum alternations was the total number of arm entries minus 2. The percentage of alternation was calculated as the number of alternations divided by maximum alternations and multiplied by 100.

Statistical Analysis: The percentage of alternation and total arm entries were expressed as the mean±SEM. The statistical significance between the normal group and the control group was calculated using the Student's t test. The statistical analysis for drug treatment versus the control group was conducted using Dunnett's multiple comparison test. The level of statistical significance was $p<0.05$.

Results

Figure 1B:
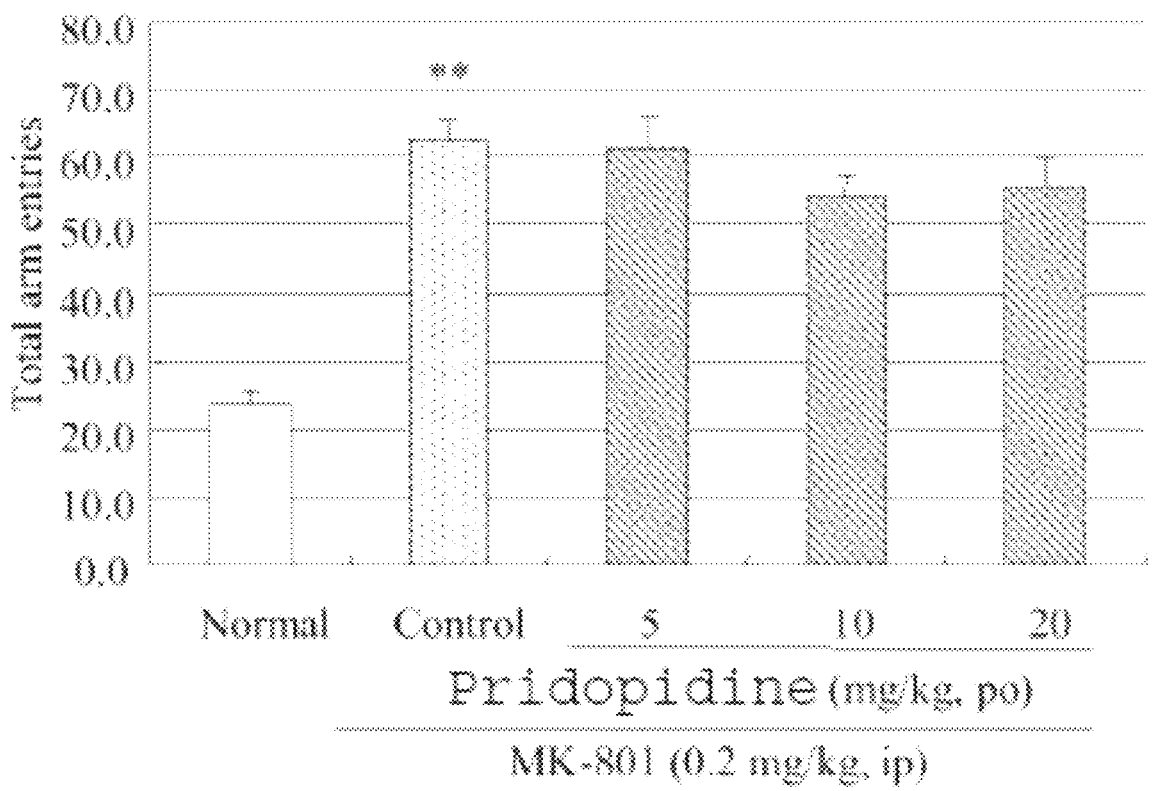
Figure 2:
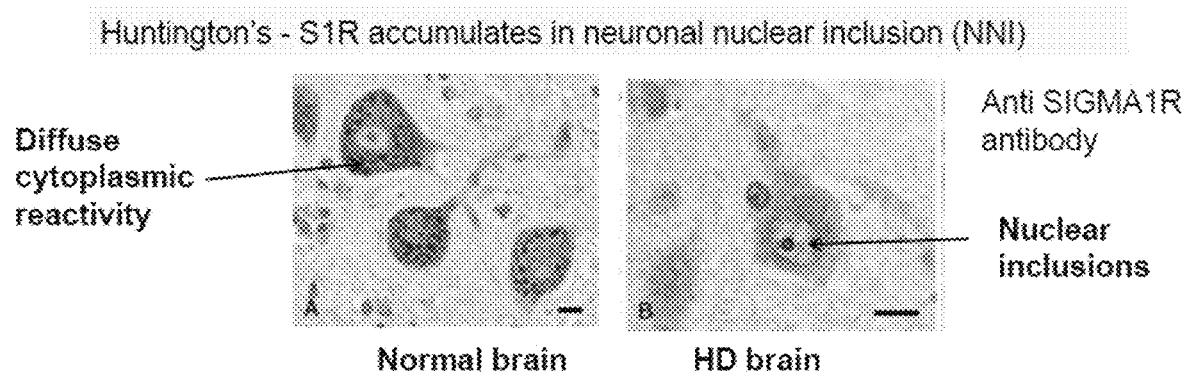
FIG. 2: Huntington's Disease S1R accumulates in neuronal nuclear inclusion (NNI).

Administration of MK-801 significantly ($P<0.01$, FIG. 1A, using the Student's t test) decreased the alternation percentage. Pridopidine restored the alternation percentage in the MK-801-treated mice with statistical significance at 10 and 20 mg/kg ($P<0.05$, FIG. 1A, by Dunnett's multiple comparison test). The total number of arm entries was significantly ($P<0.01$, FIG. 1B, using Student's t test) augmented by treatment with MK-801. Pridopidine showed no statistically significant change in the MK-801-induced increase in the total number of arm entries (FIG. 1B).

Discussion

In the Y-maze, the non-competitive NMDA antagonist, MK-801 (dizocilpine), impairs spontaneous alternation behavior, which reflects working memory, and enhances the total number of arm entries, which represents locomotor activity (Parada-Turska and Turski, 1990).

Example 1 demonstrates the anti-amnesic effects of pridopidine on working memory impairment related to the NMDA receptor blockade. Pridopidine attenuated the MK-801-induced decrease in percent alternation with statistical significance at 10 and 20 mg/kg. These results demonstrate that pridopidine improves cognitive status and improves cognitive impairment (such as working memory) in patients, including patients with cognitive deficits.

Nilsson 2004 showed that pridopidine counteracted the behavioral primitivization induced by MK-801 in mice. However, the experiments completed in Nilsson 2004 are different from the experiment described in Example 1. Specifically, the experiments completed in Nilsson 2004 did not show that pridopidine can improve cognitive function or memory loss.

Example 1 uses a Y-maze which, as described above, is a commonly used experiment to measure cognitive and memory function. In the Y-maze experiment, the ability of the rodent to use its cognitive function to remember which arm of the Y-maze it traveled to previously is tested when measuring percentage of alternation. In comparison, the experiment in Nilsson 2004 (and further described in Nilsson 2001) does not contain such a memory component. The experiment in Nilsson 2004 placed rodents in a rectangle shaped arena and used a camera to measure the movements and behavior of the mice. The specific behaviors measured were forward locomotion, rearing with exploratory sniffing, grooming and digging. In Nilsson 2004 and Nilsson 2001 treating mice with MK-801 prior to the experiment causes mice that naturally alternate between the specific measured behaviors to mostly perform monotonous forward locomotion (Nilsson 2001). What Nilsson 2004 found was that pridopidine counteracted such effects of MK-801 on mice. However, there is no clear relationship between the measured behaviors and cognitive function in the experiment of Nilsson 2004. Thus, the experiments shown in Nilsson 2004 cannot show that pridopidine enhances cognitive function. This is likely why the authors of Nilsson 2004 state that additional tests are necessary to determine if pridopidine can enhance cognitive function.

Example 2: Assessment of Efficacy of Pridopidine for Treating Patients Afflicted with Schizophrenia Periodic (e.g., daily or twice daily) oral administration of pridopidine is effective in treating human patients afflicted with schizophrenia. Periodic (e.g., daily or twice daily) oral administration of pridopidine is effective to reduce cognitive deficits associated with schizophrenia in the subject.

A pridopidine composition as described herein is administered orally to a subject suffering from schizophrenia. The administration of the composition is effective to treat the subject suffering from schizophrenia. The administration of the composition is also effective to reduce cognitive deficits associated with schizophrenia in the subject.

Example 3: Assessment of Efficacy of Pridopidine for Treating Patients Afflicted with Autism Periodic (e.g., daily or twice daily) oral administration of pridopidine is effective in treating human patients afflicted with autism. Periodic (e.g., daily or twice daily) oral administration of pridopidine is effective to reduce cognitive deficits associated with autism in the subject.

A pridopidine composition as described herein is administered orally to a subject suffering from autism. The administration of the composition is effective to treat the subject suffering from autism. The administration of the composition is also effective to reduce cognitive deficits associated with autism in the subject.

Example 4: Assessment of Efficacy of Pridopidine for Treating Patients Afflicted with Epilepsy Periodic (e.g., daily or twice daily) oral administration of pridopidine is effective in treating human patients afflicted with epilepsy. Periodic (e.g., daily or twice daily) oral administration of pridopidine is effective to reduce cognitive deficits associated with epilepsy in the subject.

A pridopidine composition as described herein is administered orally to a subject suffering from epilepsy. The administration of the composition is effective to treat the subject suffering from epilepsy. The administration of the composition is also effective to reduce cognitive deficits associated with epilepsy in the subject.

Example 5: Assessment of Efficacy of Pridopidine for Treating Patients Afflicted with Anxiety Disorders Periodic (e.g., daily or twice daily) oral administration of pridopidine is effective in treating human patients afflicted with anxiety disorders. Periodic (e.g., daily or twice daily) oral administration of pridopidine is effective to reduce cognitive deficits associated with anxiety disorders in the subject.

A pridopidine composition as described herein is administered orally to a subject suffering from an anxiety disorder. The administration of the composition is effective to treat the subject suffering from an anxiety disorder. The administration of the composition is also effective to reduce cognitive deficits associated with an anxiety disorder in the subject.

Example 6: Assessment of Efficacy of Pridopidine for Treating Patients Afflicted with Major Depressive Disorder Periodic (e.g., daily or twice daily) oral administration of pridopidine is effective in treating human patients afflicted with major depressive disorder. Periodic (e.g., daily or twice daily) oral administration of pridopidine is effective to reduce cognitive deficits associated with major depressive disorder in the subject.

A pridopidine composition as described herein is administered orally to a subject suffering from major depressive disorder. The administration of the composition is effective to treat the subject suffering from major depressive disorder. The administration of the composition is also effective to reduce cognitive deficits associated with an anxiety disorder in the subject.

Example 7: Assessment of Efficacy of Pridopidine for Treating Patients Afflicted with Parkinson's Disease Periodic (e.g., daily or twice daily) oral administration of pridopidine is effective in treating human patients afflicted with Parkinson's disease. Periodic (e.g., daily or twice daily) oral administration of pridopidine is effective to reduce cognitive deficits associated with Parkinson's disease in the subject.

A pridopidine composition as described herein is administered orally to a subject suffering from Parkinson's disease. The administration of the composition is effective to treat the subject suffering from Parkinson's disease. The administration of the composition is also effective to reduce cognitive deficits associated with Parkinson's disease in the subject.

Example 8: Assessment of Efficacy of Pridopidine for Treating Patients Afflicted with Alzheimer's Disease Periodic (e.g., daily or twice daily) oral administration of pridopidine is effective in treating human patients afflicted with Alzheimer's disease. Periodic (e.g., daily or twice daily) oral administration of pridopidine is effective to reduce cognitive deficits associated with Alzheimer's disease in the subject.

A pridopidine composition as described herein is administered orally to a subject suffering from Alzheimer's disease. The administration of the composition is effective to treat the subject suffering from Alzheimer's disease. The administration of the composition is also effective to reduce cognitive deficits associated with Alzheimer's disease in the subject.

Example 9: Assessment of Efficacy of Pridopidine for Treating Patients Afflicted with Tardive Dyskinesia Periodic (e.g., daily or twice daily) oral administration of pridopidine is effective in treating human patients afflicted with tardive dyskinesia. Periodic (e.g., daily or twice daily) oral administration of pridopidine is effective to reduce cognitive deficits associated with tardive dyskinesia in the subject.

A pridopidine composition as described herein is administered orally to a subject suffering from tardive dyskinesia. The administration of the composition is effective to treat the subject suffering from tardive dyskinesia. The administration of the composition is also effective to reduce cognitive deficits associated with tardive dyskinesia in the subject.

Example 10: Assessment of Efficacy of Pridopidine for Treating Patients Afflicted with Depression Periodic (e.g., daily or twice daily) oral administration of pridopidine is effective in treating human patients afflicted with Depression. Periodic (e.g., daily or twice daily) oral administration of pridopidine is effective to reduce cognitive deficits associated with Depression in the subject.

A pridopidine composition as described herein is administered orally to a subject suffering from Depression. The administration of the composition is effective to treat the subject suffering from Depression. The administration of the composition is also effective to reduce cognitive deficits associated with Depression in the subject.

Example 11: Assessment of Efficacy of Pridopidine for Treating Patients Afflicted with Sickle Cell Anemia Periodic (e.g., daily or twice daily) oral administration of pridopidine is effective in treating human patients afflicted with sickle cell anemia. Periodic (e.g., daily or twice daily) oral administration of pridopidine is effective to reduce cognitive deficits associated with sickle cell anemia in the subject.

A pridopidine composition as described herein is administered orally to a subject suffering from sickle cell anemia. The administration of the composition is effective to treat the subject suffering from sickle cell anemia. The administration of the composition is also effective to reduce cognitive deficits associated with sickle cell anemia in the subject.

Example 12: Assessment of Efficacy of Pridopidine for Treating Patients Afflicted with Stroke Periodic (e.g., daily or twice daily) oral administration of pridopidine is effective in treating human patients after having a stroke. Periodic (e.g., daily or twice daily) oral administration of pridopidine is effective to reduce cognitive deficits associated with stroke in the subject.

A pridopidine composition as described herein is administered orally to a subject after suffering from a stroke. The administration of the composition is effective to treat the subject after suffering from a stroke. The administration of the composition is also effective to reduce cognitive deficits associated with stroke in the subject.

Example 13: Assessment of Efficacy of Pridopidine for Treating Patients Afflicted with Chronic Pain Syndrome Periodic (e.g., daily or twice daily) oral administration of pridopidine is effective in treating human patients afflicted with chronic pain syndrome. Periodic (e.g., daily or twice daily) oral administration of pridopidine is effective to reduce cognitive deficits associated with chronic pain syndrome in the subject.

A pridopidine composition as described herein is administered orally to a subject suffering from chronic pain syndrome. The administration of the composition is effective to treat the subject suffering from chronic pain syndrome. The administration of the composition is also effective to reduce cognitive deficits associated with chronic pain syndrome in the subject.

Example 14: Assessment of Efficacy of Pridopidine for Treating Patients Afflicted with Addiction Periodic (e.g., daily or twice daily) oral administration of pridopidine is effective in treating human patients afflicted with addiction. Periodic (e.g., daily or twice daily) oral administration of pridopidine is effective to reduce cognitive deficits associated with addiction in the subject.

A pridopidine composition as described herein is administered orally to a subject suffering from addiction. The administration of the composition is effective to treat the subject suffering from addiction. The administration of the composition is also effective to reduce cognitive deficits associated with addiction in the subject.

Example 15: Assessment of Efficacy of Pridopidine for Treating Patients Afflicted with Huntington's Disease Periodic (e.g., daily or twice daily) oral administration of pridopidine is effective in treating human patients afflicted with Huntington's disease. Periodic (e.g., daily or twice daily) oral administration of pridopidine is effective to reduce cognitive deficits associated with Huntington's disease in the subject.

A pridopidine composition as described herein is administered orally to a subject suffering from Huntington's disease. The administration of the composition is effective to treat the subject suffering from Huntington's disease. The administration of the composition is also effective to reduce cognitive deficits associated with Huntington's disease in the subject.

Example 16

Alteration in the density of spines and abnormalities in the size and shape of spines was observed in the brains of HD patients (Graveland 1985).

Figure 3:
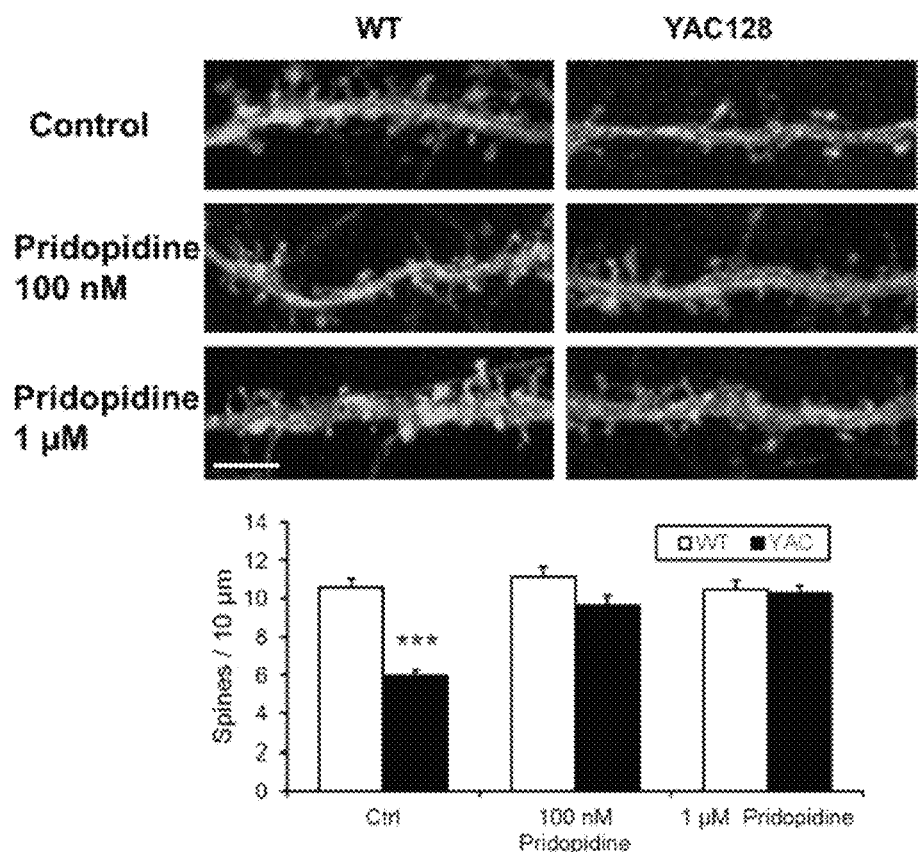
FIG. 3: Pridopidine rescues spine loss in YAC128 corticostriatal co-cultures.
Figure 4:
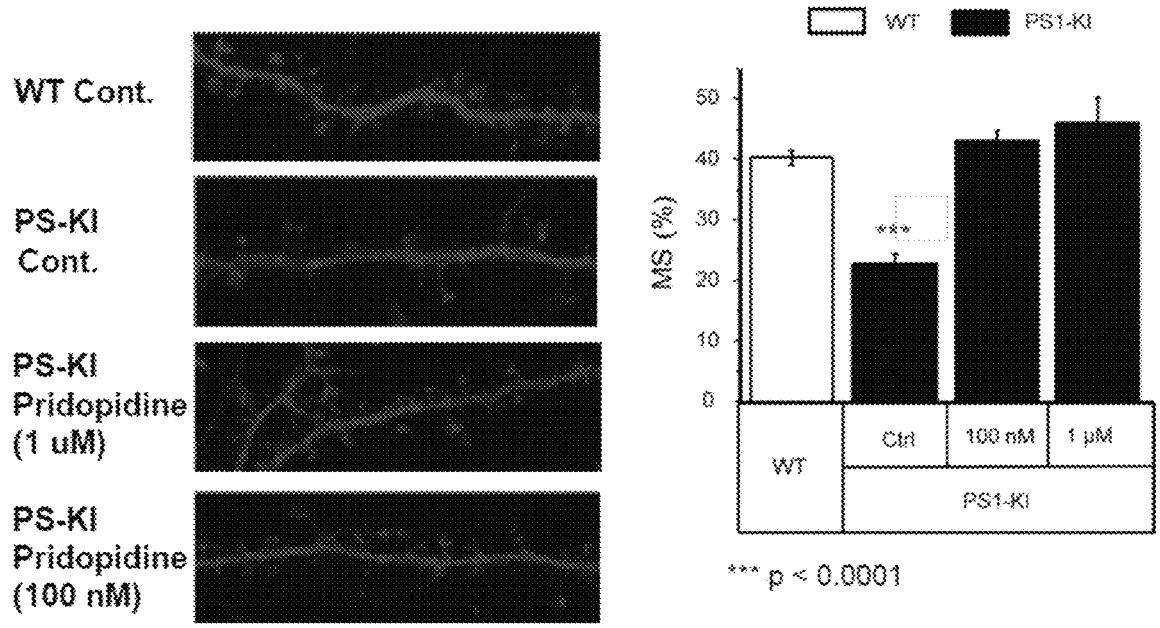
FIG. 4: Pridopidine rescues mushroom spine loss in PS-KI (AD) neurons.

FIG. 3 shows that pridopidine rescues spine loss in YAC128 corticostriatal co-cultures. FIG. 4 shows that pridopidine rescues mushroom spine loss in PS-KI (AD) neurons.

Dendritic spines are important in maintaining cognition and motor functions. Dendritic spine formation is critical for the establishment of excitatory synaptic networks. Spines show structural plasticity as the basis for the physiological changes in synaptic efficacy that underlie learning and memory. Motor control is regulated by cortical-medium spiny neurons synaptic connections. The spines are the basis for these connections (Kreitzer 2008 and Bourne 2008).

Example 17: Acetylcholine and Pridopidine

Animals: Eighteen adult male Sprague Dawley rats (Harlan, USA) were used. Before the experiment, rats were group housed in plastic cages (3-4 animals/cage) and had access to food and water ad libitum. Animals were kept on a 12/12 hour light/dark cycle. Experiments were conducted in accordance with the protocols approved by the Institutional Animal Care and Use Committee of Brains On-Line, LLC.

Microdialysis Experiment: Microdialyis experiments were performed one day after surgery. On the day of the experiment, the probes were connected with flexible PEEK tubing to a microperfusion pump (Harvard PHD 2000 Syringe pump, Holliston, Mass. or similar). Microdialysis probes were perfused with aCSF containing 147 mM NaCl, 3.0 mM KCl, 1.2 mM CaCl2) and 1.2 mM MgCl2, at a flow rate of 1.5 µL/min. Microdialysis samples were collected in 30 minute periods by an automated fraction collector (820 Microsampler, Univentor, Malta) into 300 µL polystryene mini-vials already containing 15 µL 0.02 M formic acid (FA) and 0.04% ascorbic acid in ultrapurified $H_2O$. Four basal samples were collected before pridopidine (15 or 60 mg/kg, PO) or vehicle was administered. Samples were collected.

Results: Acetylcholine (Ach) Levels in Dialysate

Figure 5:
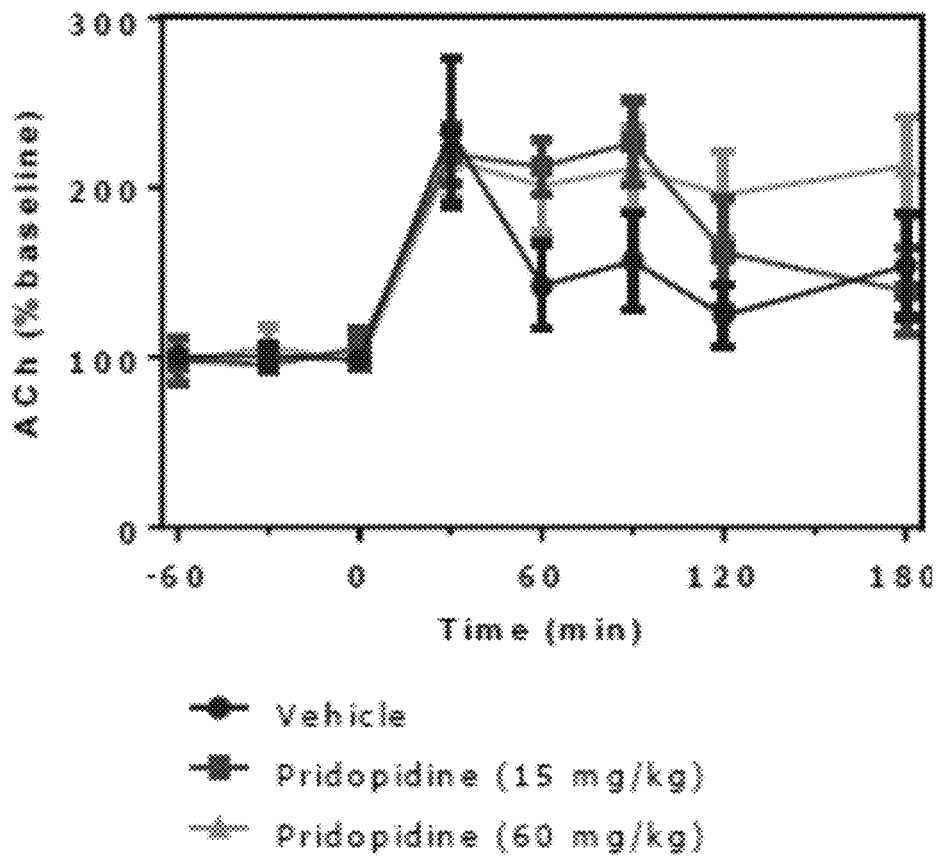
FIG. 5: Effect of pridopidine (15 and 60 mg/kg) on Acetylcholine (Ach) levels in the PFC of rats (data expressed as mean % baseline±SEM).
Figure 6:
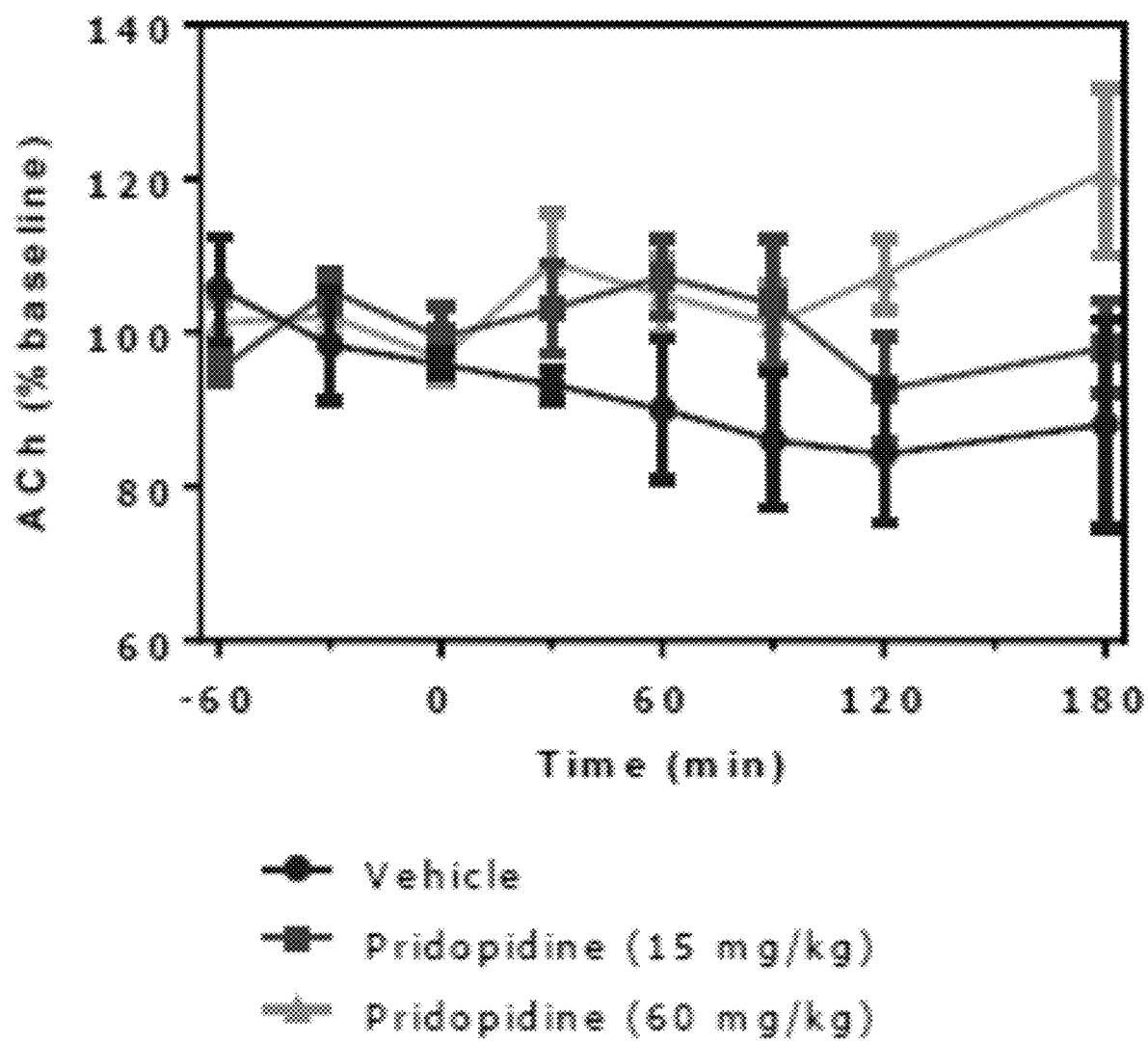
FIG. 6: Effect of Pridopidine (15 and 60 mg/kg) on ACh levels in the STR of rats (data expressed as mean % baseline±SEM).
Figure 7:
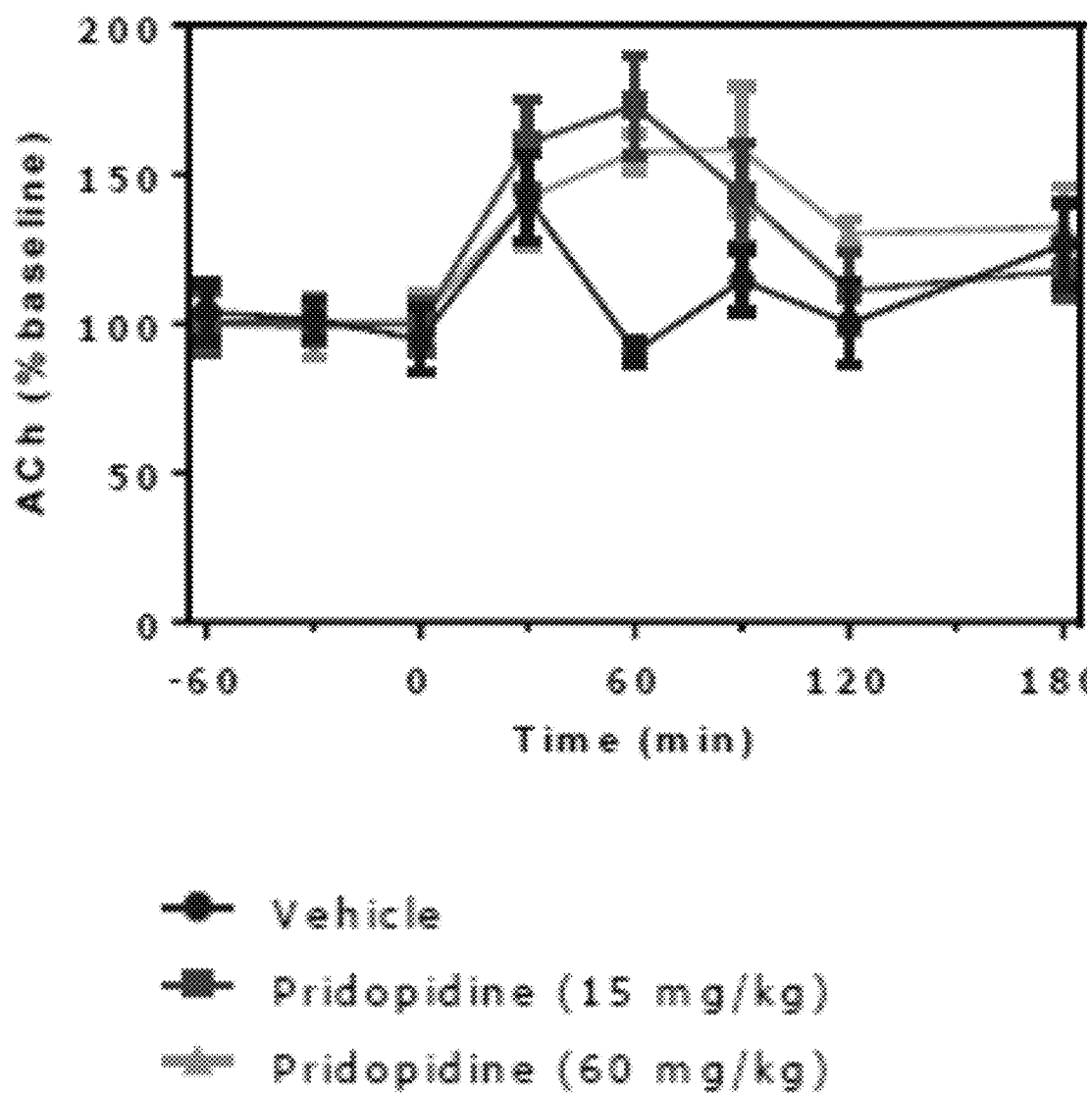
FIG. 7: Effect of pridopidine (15 and 60 mg/kg) on ACh levels in the Hipp of rats (data expressed as mean % baseline±SEM).

FIGS. 5, 6, and 7 show the levels of ACh in the prefrontal cortex (PFC), striatum (STR), and hippocampus (Hipp), respectively. Treatment with pridopidine resulted in significant increases in Ach in the prefrontal cortex following 15 mg/kg administration at 30 min after administration (219% change from baseline; p<0.05), at 60 min after administration (226% change from baseline; p<0.05) and at 90 min after administration (226% change from baseline; p<0.05), and following 60 mg/kg administration at 30 min after administration (215% change from baseline; p<0.05), at 60 min after administration (201% change from baseline; p<0.05), at 90 min after administration (211% change from baseline; p<0.05) and at 180 min after administration (212% change from baseline; p<0.05). Treatment with pridopidine resulted in significant increases in Ach in the hippocampus following 15 mg/kg administration at 30 min after administration (160% change from baseline; p<0.05) and at 60 min after administration (173% change from baseline; p<0.05), and following 60 mg/kg administration at 60 min after administration (157% change from baseline; p<0.05) and at 90 min after administration (158% change from baseline; p<0.05) Tables 1 and 2 present the Maximum % Change from baseline in Ach levels after 15 and 60 mg/kg administration, respectively.

TABLE 1

Acetylcholine levels in dialysate (% Change from baseline. Single dose 15 mg/kg p.o)

|  | Striatum | Prefrontal cortex | Hippocampus |
|---|---|---|---|
| Acetylcholine | 107 | 226* | 173* |

*statistically significant (p < 0.05)

TABLE 2

Acetylcholine levels in dialysate (% Change from baseline. Single dose 60 mg/kg p.o)

|  | Striatum | Prefrontal cortex | Hippocampus |
|---|---|---|---|
| Acetylcholine | 120 | 215* | 158* |

*statistically significant (p < 0.05)

Acetylcholine is an important neurotransmitter in the nervous system and is necessary for learning and memory function (Winkler 1995). Acetylcholine has been accorded an important role in supporting learning and memory processes in the hippocampus. Cholinergic activity in the hippocampus and prefrontal cortex is correlated with memory (Hironaka 2001). Additionally, restoration of ACh in the hippocampus after disruption of the septohippocampal pathway is sufficient to rescue memory (Parent 2004).

Example 18: Effect of Pridopidine in a Model of AD: Injury of Rat Primary Cortical Neurons by Human Amyloid Beta 1-42

AD is characterized by the progressive accumulation of intracellular neurofibrillary tangles, extracellular parenchymal senile plaques, and cerebrovascular deposits comprised of amyloid-β 1-42 peptides (Sakono et al, 2010).

A β peptide is a proteolytic product derived through sequential proteolysis of amyloid precursor protein (APP), which occurs as a result of cleavage by β-secretase and γ-secretase. Mutations at the cleavage sites in APP increase the production of A β oligomers. The progressive accumulation of Aβ in the form of senile plaques, which is one of the pathologic hallmarks of AD, had been recognized as one of the major causes of AD pathology (Kawahara and Kuroda, 2000) by triggering neurotoxicity, oxidative damage, and inflammation (Pike et al., 1991; Cummings et al., 1998; Combs et al., 2000). The most abundant Aβ peptide form found in AD brain senile plaques are the 40 and 42 amino acid forms (Sisodia et al., 1990).

However, the number of senile plaques in a particular region of the AD brain correlates poorly with the local extent of neuron death or synaptic loss, or with cognitive impairment. Recent studies show a robust correlation between the soluble Aβ oligomer (AβO) levels and the extent of synaptic loss and severity of cognitive impairment (for review see Sakono et al., 2010).

The study investigated the neuroprotective effect of pridopidine on cortical neurons incubated for 24 hours in the presence of AβO, an in vitro model of AD (Callizot et al., 2013). BDNF at 50 ng/ml was used as a positive control in this study.

Experimental Protocol

Cortical Neurons Cell Culture

Rat cortical neurons were cultured as follows. Pregnant female rats of 15 days gestation were killed by cervical dislocation (Rats Wistar; Janvier Lab) and the fetuses were removed from the uterus. The cortexes were removed and placed in ice-cold medium of Leibovitz (L15, Panbiotech, ref: P04-27055) containing 2% of Penicillin 10.000 U/ml and Streptomycin 10 mg/ml (PS, Panbiotech, ref: P06-07100) and 1% of Bovine Serum Albumin (BSA, Panbiotech, Ref: P06-1391100). Cortexes were dissociated by trypsin-EDTA (Panbiotech, Ref: P10-023100) for 20 min at 37° C. The reaction was stopped by the addition of Dulbecco's modified Eagle's Medium (DMEM, Panbiotech, Ref P04-03600) containing DNase1 grade II (0.1 mg/ml, Panbiotech, ref: P60-37780100) and 10% of Foetal Calf Serum (FCS, Invitrogen, ref: 10270-098). Cells were then mechanically dissociated by 3 serial passages through a 10 ml pipette. Cells were then centrifuged at 515×g for 10 min at 4° C. The supernatant was discarded and the pellet of cells was re-suspended in a defined culture medium consisting of Neurobasal (Nb, Invitrogen, ref: 21103) supplemented with B27 (20%, Invitrogen, ref: 17504), L-glutamine (2 mM, Panbiotech, ref: P04-80100), 2% of PS solution and 10 ng/ml of Brain-derived neurotrophic factor (BDNF, PanBiotech, Ref: CB-1115002). Viable cells were counted in a Neubauer cytometer using the trypan blue exclusion test. The cells were seeded at a density of 30,000 cells/well in 96 well-plates pre-coated with poly-L-lysine (Greiner ref: 655930) and were cultured at +37° C. in a humidified air (95%)/$CO_2$ (5%) atmosphere.

After 11 days of culture, cortical neurons were intoxicated with human Aβ 1-42 at 10 µM for 24 hrs.

One culture was performed per condition, 6 wells per condition.

Pridopidine and Human β Amyloid 1-42 Treatment

The human β amyloid 1-42 peptide preparation was done following an internal and original procedure validated by Neuron experts (Callizot et al., 2013). Briefly, on day 12 of culture, the supernatant was removed and fresh medium was added, with human amyloid β 1-42 (10 µM) and with pridopidine.

The following conditions were included:
a) Medium without Human β amyloid 1-42 (control) for 24 h
b) Human β amyloid 1-42 (10 µM) for 24 h
c) Human β amyloid 1-42 (10 µM) for 24 h with pridopidine (200, 50, 10, 1, 0.1 and 0.01 µM)
d) Human β amyloid 1-42 (10 µM) for 24 h with BDNF (50 ng/ml)

End Point Evaluation: Measure of Total Number of MAP 2 Neurons.

Neurons that survived after 24 h incubation were stained with MAP 2.

After 24 hours, cells were washed twice in Phosphate Buffered Saline (PBS, PanBiotech, ref: P04-36500) and then fixed by a cold solution of ethanol (95%, Sigma, ref: 32221) and acetic acid (5%, Sigma, ref: 33209) for 5 min. The cells were then permeabilized and non-specific sites were blocked with a solution of PBS containing 0.1% of saponin (Sigma Aldrich, ref: S7900) and 1% FCS for 15 min at room temperature. Then, cells were incubated for 2 hours with mouse monoclonal primary Microtubule-associated protein 2 antibody (MAP-2, Sigma M4403) for 2 hours in the same solution at the dilution of 1/400. This antibody was revealed with Alexa Fluor 488 goat anti-mouse (Molecular probe, ref: A 11001) for 1 hour in the same solution.

Nuclei of cells were labelled by a fluorescent marker (Hoechst solution, SIGMA, ref: B1155).

For each condition, 20 pictures per well were taken using InCell Analyzer™ 2000 (GE Healthcare) with 20× magnification. All images were taken under the same conditions.

Statistics

The data were expressed as mean±s.e.mean (of 6 or 12 data per condition). A global analysis of the data was performed using a one-way analysis of variance (ANOVA). *$p<0.05$; $p<0.01$; *$p<0.005$.

Figure 8:
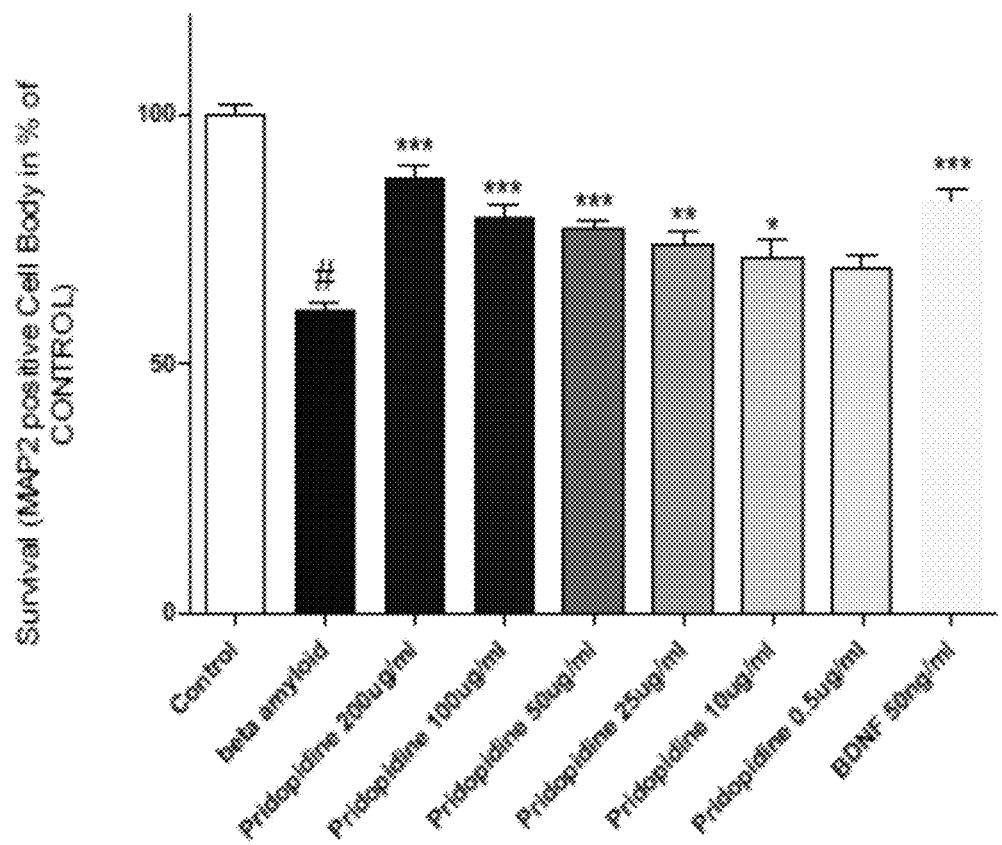
FIG. 8: Effect of pridopidine (6 concentrations) and BDNF (50 ng/ml) on survival of primary neuron cultured in the presence of β amyloid 1-42 (10 μM), expressed in percentage of control (mean±s.e.m; *$p<0.05$; $p<0.01$; *$p<0.005$; β amyloid 1-42 vs pridopidine/BDNF; one way Anova followed by Dunnett's test).

Results

β amyloid 1-42 injury applied at 10 µM for 24 h induced a large and significant decrease (~40%, $p<0.005$) in MAP 2 positive cells (FIG. 8).

Application of reference compound BDNF (50 ng/ml) inhibited cell death resulting from β amyloid 1-42 injury. These results validate the study.

Pridopidine reduced the toxic effect of β amyloid 1-42 in a dose dependent manner. The proportion of neuron survival was 87% of the medium control when incubated with pridopidine at 200 µg/ml ($p<0.005$). At 100, 50, 25 and 10 µg/ml pridopidine increased significantly neuron survival resulting from β amyloid 1-42 injury (79%, $p<0.005$; 77% $p<0.005$; 74% $p<0.01$ and 71%, $p<0.05$, respectively).

Conclusions

Pridopidine increased neuron survival resulting from β amyloid 1-42 injury significantly and with a dose dependent manner.

Example 19: Pridopidine Selectively Occupies the S1R in Humans at Low Dose

Figure 9:
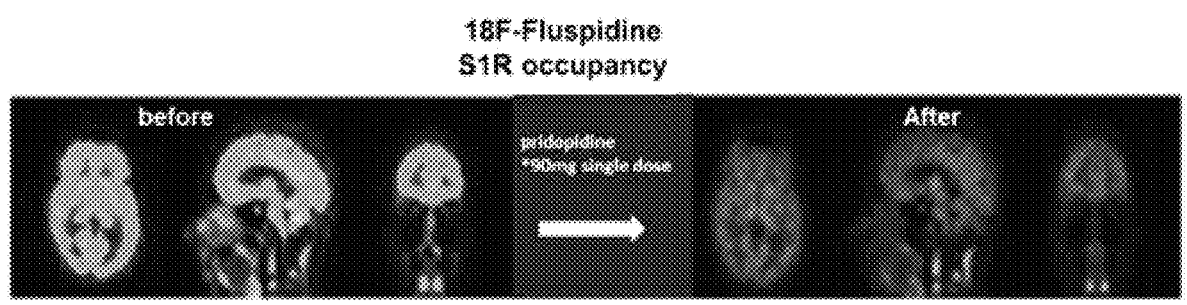
FIG. 9: Pridopidine low dose shows full SiR occupancy in a Human PET Study and complete 18F-Fluspidine displacement after single oral dose of 90 mg pridopidine.

Receptor Occupancy (RO) of pridopidine to the S1R and D2R was evaluated using Positron Emission Tomography (PET) imaging in the human brain (healthy volunteers and HD patients). The radio ligand (S)-(−)-[18F]fluspidine was used to image S1Rs, and the radio ligand [18F]fallypride was used to image D2Rs. The results of the imaging analysis show that at a plasma exposure correlating to the 45 mg bid dose steady state (ss) exposure, (90 mg single dose), pridopidine fully occupies the S1R (>90%) (FIG. 9).

Figure 10:
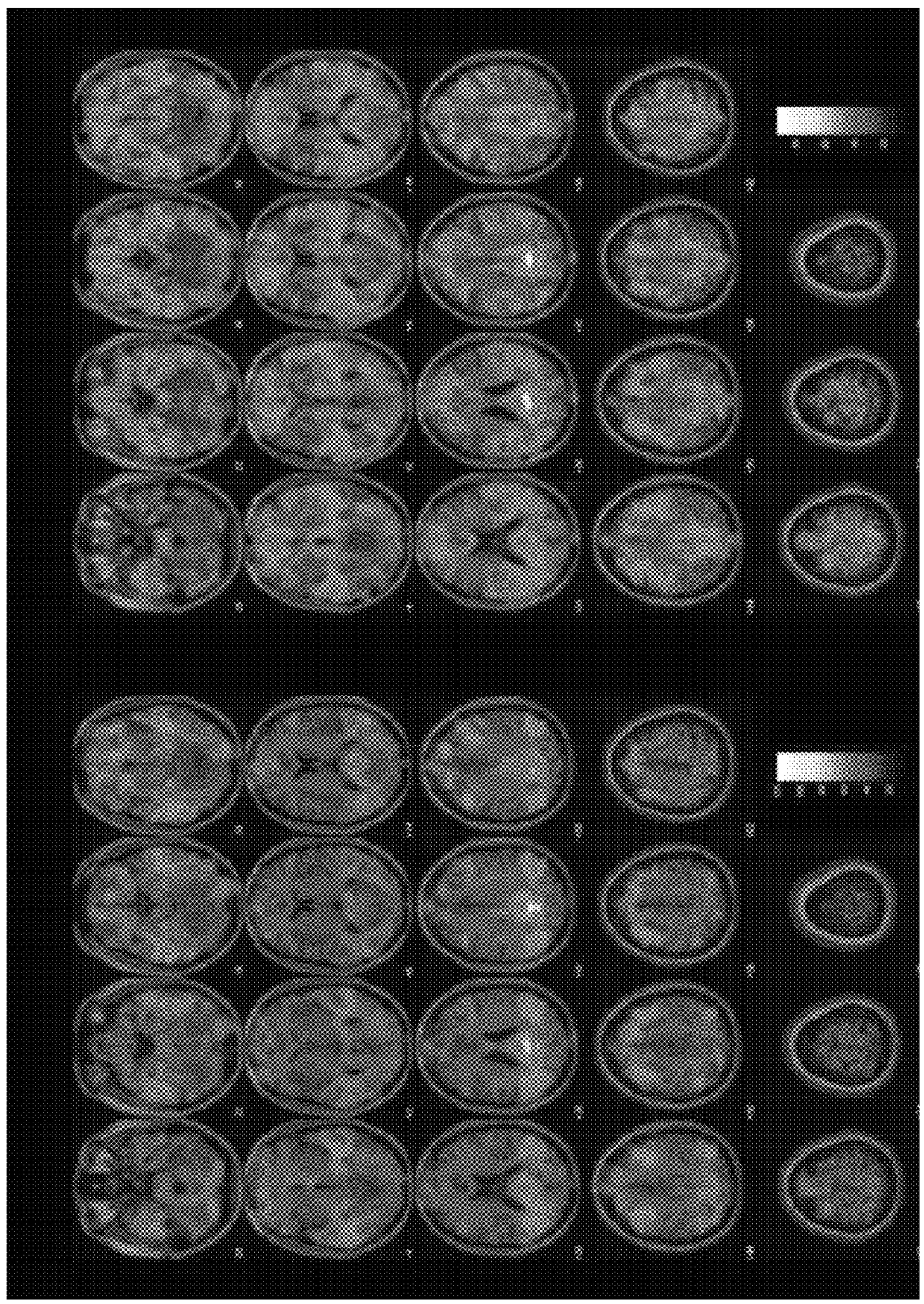
FIG. 10: The functional connectivity within the DMN with/without 90 mg pridopidine in HV (correlates with exposure at 45 mg bid at steady state). Upper panel: four individuals after 90 mg single dose pridopidine (post). Lower panel four individuals without pridopidine treatment (pre).
Figure 11:
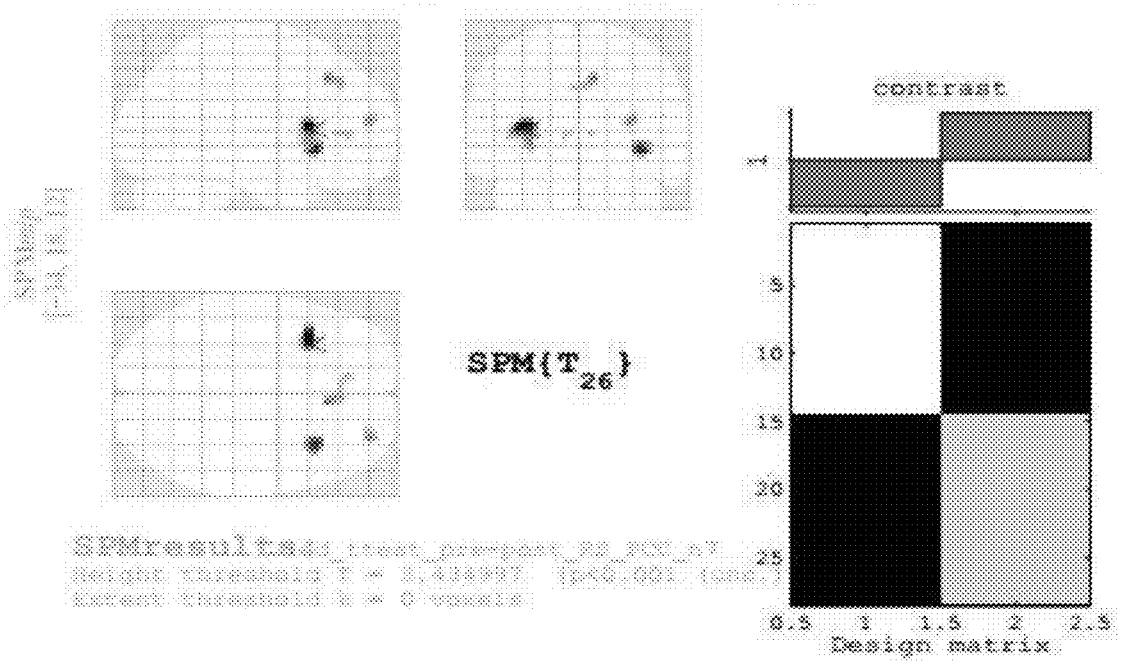
FIG. 11: SPM-based voxelwise group comparison (within the DMN) in HV before (pre) and after (post) 90 mg pridopidine (correlates with exposure at 45 mg bid at steady state) reveals pridopidine increased FC in the insula.
Figure 12:
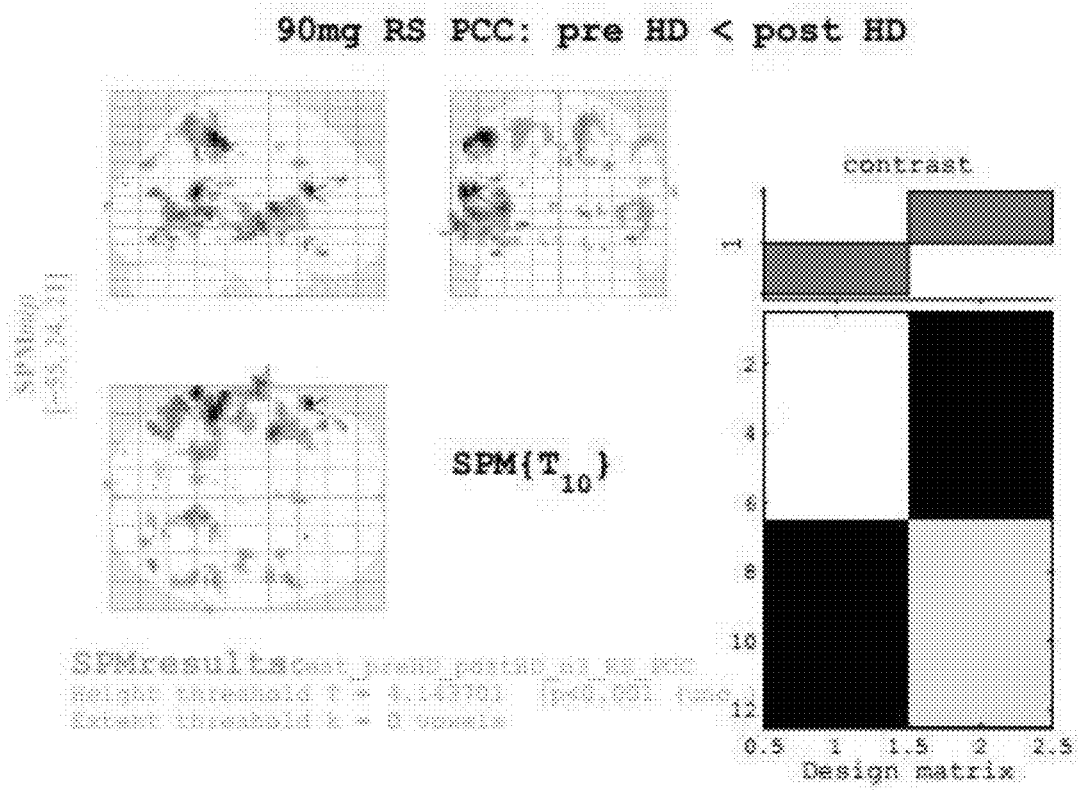
FIG. 12: SPM-based voxelwise group comparison (within the DMN) in HD patients before (pre) and after (post) 90 mg pridopidine (correlates with exposure at 45 mg bid at steady state) reveals pridopidine increased FC in the parietal and temporal cortex as well as precuneus and insula.

Example 20: Pridopidine's S1R/D2R Occupancy and Brain Network Activity Demonstrates Correlation Correlation between S1R/D2R occupancy and brain network activity was evaluated using the functional resting-state MRI (rs-fMRI). Functional connectivity (FC) was calculated from rs-fMRI data sets. Pridopidine low dose (correlating to ss plasma exposure at 45 mg bid dose), shown by PET to selectively occupy only the S1R (no D2R binding), led to an increase in the DMN connectivity (increased activity) in healthy volunteers and in HD patients, as demonstrated in FIGS. 10-12. FIG. 10 shows pridopidine increases FC within the DMN in healthy volunteers (HVs). This visual inspection result is supported by the results of the SPM-based voxelwise group comparison: FIG. 11: SPM-based voxelwise group comparison (within the DMN) in HV before (pre) and after (post) 90 mg pridopidine reveals pridopidine increased FC in the insula. FIG. 12: SPM-based voxelwise group comparison (within the DMN) in HD patients before (pre) and after (post) 90 mg pridopidine reveals pridopidine increased FC in the parietal and temporal cortex as well as precuneus and insula.

Pridopidine showed an unexpected increase in DMN at low dose which selectively occupies the S1R.

REFERENCES

A Hyrskyluoto et al, Cell Death and Disease (2013) 2013.

Agosta, F., Pievani, M., Geroldi, C., Copetti, M., Frisoni, G. B., & Filippi, M. (2012). Resting state fMRI in Alzheimer's disease: Beyond the default mode network. Neurobiology of Aging, 33(8), 1564-1578.

Anatol C. Kreitzer and Robert C. Malenka Neuron. 2008

Balthazar, M., Weiler, M., Campos, B., Rezende, T. J., Damasceno, B., & Cendes, F. (2014). Alzheimer'S As a Default Mode Network Disease: a Grey Matter, Functional, and Structural Connectivity Study. Alzheimer's & Dementia, 10(4), P391. https://doi.org/10.1016/j.jalz.2014.05.476

Bonnelle, V., Ham, T. E., Leech, R., Kinnunen, K. M., Mehta, M. A., Greenwood, R. J., & Sharp, D. J. (2012). Salience network integrity predicts default mode network function after traumatic brain injury. Proceedings of the National Academy of Sciences of the United States of America, 109(12), 4690-4695.

Brier, M. R., Thomas, J. B., & Ances, B. M. (2014). Network dysfunction in Alzheimer's disease: refining the disconnection hypothesis. Brain Connectivity, 4(5), 299-311. https://doi.org/10.1089/brain.2014.0236

Brito et al, Cell Death Dis, 2013.

Buckner, R. L., Andrews-Hanna, J. R., & Schacter, D. L. (2008). The brain's default network: Anatomy, function, and relevance to disease. Annals of the New York Academy of Sciences, 1124, 1-38. https://doi.org/10.1196/annals.1440.011

Callizot N, Combes M, Steinschneider R, Poindron P. Operational dissection of β-amyloid cytopathic effects on cultured neurons. J Neurosci Res. (2013); May; 91(5): 706-16.

Combs C K, Johnson D E, Karlo J C, Cannady S B, Landreth G E. Inflammatory mechanisms in Alzheimer's disease: inhibition of beta-amyloid-stimulated pro-inflammatory responses and neurotoxicity by PPARgamma agonists. J Neurosci. (2000); 20(2):558-67.

Coyle J T, Tsai G. NMDA receptor function, neuroplasticity, and the pathophysiology of schizophrenia. Int Rev Neurobiol 2004; 59:491-515.

Cumming T B, et al. Stroke, cognitive deficits, and rehabilitation: still an incomplete picture. Int J Stroke. 2013 January; 8(1):38-45.

Cummings J L, Vinters H V, Cole G M, Khachaturian Z S. Alzheimer's disease: etiologies, pathophysiology, cognitive reserve, and treatment opportunities. Neurology. (1998); 51(1 Suppl 1):S2-17; discussion S65-7.

David M Dietz et al., AFosB Induction in Prefrontal Cortex by Antipsychotic Drugs is Associated with Negative Behavioral Outcomes. Neuropsychopharmacology (2014) 39, 538-544.

Desgranges, B., Mevel, K., Chetelat, G., & Eustache, F. (2011). The default mode network in healthy aging and Alzheimer's disease. International Journal of Alzheimer's Disease, 2011. https://doi.org/10.4061/2011/535816

Detrait E et al. Automation of Continuous Spontaneous Alternation to Increase the Throughput for In Vivo Screening of Cognitive Enhancers. Optimization of the Ethovision System for the Y-maze Test in Mice. Proceedings of Measuring Behavior 2010 (Eindhoven, The Netherlands, Aug. 24-27, 2010).

Dubois B and Pillon B, Cognitive deficits in Parkinson's disease. J Neurol. 1997 January; 244(1):2-8.

Ferreri F et al. Current research on cognitive aspects of anxiety disorders. Current Opinion in Psychiatry 2011, 24:49-54

Fioravanti M. Cognitive deficits in schizophrenia: an updated metanalysis of the scientific evidence. Fioravanti et al. BMC Psychiatry 2012, 12:64

Foroud T et al. Cognitive scores in carriers of Huntington's disease gene compared to noncarriers. Ann Neurol. 1995 May; 37(5):657-64.

Francardo et al, Brain, 2014.

Fujimoto M1, Hayashi T, Urfer R, Mita S, Su T P. "Sigma-1 receptor chaperones regulate the secretion of brain-derived neurotrophic factor." Synapse. 2012 July; 66(7): 630-9.

Ghosh, B. C. P., Calder, A. J., Peers, P. V., Lawrence, A. D., Acosta-Cabronero, J., Pereira, J. M., . . . Rowe, J. B. (2012). Social cognitive deficits and their neural correlates in progressive supranuclear palsy. Brain, 135(7), 2089-2102. https://doi.org/10.1093/brain/aws128

Girardi, A., MacPherson, S. E., & Abrahams, S. (2011). Deficits in Emotional and Social Cognition in Amyotrophic Lateral Sclerosis. Neuropsychology, 25(1), 53-65.

Gould T, Addiction and Cognition. Addiction science & clinical Practice—December 2010.

Graveland, G A, et al. Evidence for degenerative and regenerative changes in neostriatal spiny neurons in Huntington's disease. Science. 1985 Feb. 15; 227(4688):770-3.

Guye, M., Bettus, G., Bartolomei, F., & Cozzone, P. J. (2010). Graph theoretical analysis of structural and functional connectivity MRI in normal and pathological brain networks. Magnetic Resonance Materials in Physics, Biology and Medicine, 23(5-6), 409-421. https://doi.org/10.1007/s 10334-010-0205-z Hart R et al., Cognitive Impairment in Patients With Chronic Pain: The Significance of Stress. Current Pain and Headache Reports 2003, 7:116-226.

Hazim A et al. The effects on motor behaviour and short-term memory tasks in mice following an acute administration of Mitragyna speciosa alkaloid extract and mitragynine Journal of Medicinal Plants Research Vol. 5(24), pp. 5810-5817, 30 Oct. 2011.

Hironaka N, Tanaka K, Izaki Y, Hori K, Nomura M. Memory-related acetylcholine efflux from rat prefrontal cortex and hippocampus: a microdialysis study. Brain Res. 2001 May 18; 901(1-2):143-50.

Hyungju Park and Mu-ming Poo, NATURE REVIEWS NEUROSCIENCE 2013

Ishikawa & Hashimoto, Journal of Receptor, Ligand and Channel Research 2010.

Jennifer N. Bourne and Kristen M. Harris Annu. Rev. Neurosci. 2008

Jeong-Soo Seo et al. Effect of MK-801 on the Prevention and Treatment of Tardive Dyskinesia. Korean Journal of Biological Psychiatry. Volume 4, Number 2 (February 1997).

Jonkers N, Sarre S, Ebinger G, Michotte Y., MK801 influences L-DOPA-induced dopamine release in intact and hemi-parkinson rats. Eur J Pharmacol. 2000 Nov. 3; 407(3):281-91.

Kathryn J. Bryan, Hyoung-gon Lee, George Perry, Mark A. Smith, and Gemma Casadesus. Chapter 1 Transgenic Mouse Models of Alzheimer's Disease: Behavioral Testing and Considerations. Methods of Behavior Analysis in Neuroscience. 2nd edition. (2009).

Kawahara M, Kuroda Y. Molecular mechanism of neurodegeneration induced by Alzheimer's beta-amyloid protein: channel formation and disruption of calcium homeostasis. Brain Res Bull. (2000); 53(4):389-97.

Keefe R S et al., Cognitive effects of pharmacotherapy for major depressive disorder: a systematic review. J Clin Psychiatry. 2014 August; 75(8):864-76.

Kipps, C. M., & Hodges, J. R. (2006). Theory of mind in frontotemporal dementia. Social Neuroscience, 1(3-4), 235-244. https://doi.org/10.1080/17470910600989847

Krabbendam L et al., Tardive dyskinesia is associated with impaired retrieval from long-term memory: the Curacao Extrapyramidal Syndromes Study: IV. Schizophr Res. 2000 Mar. 16; 42(1):41-6.

Lucas-Jiménez, O., Ojeda, N., Peña, J., Diez-Cirarda, M., Cabrera-Zubizarreta, A., Gomez-Esteban, J. C., . . . Ibarretxe-Bilbao, N. (2016). Altered functional connectivity in the default mode network is associated with cognitive impairment and brain anatomical changes in Parkinson's disease. Parkinsonism and Related Disorders, 33, 58-64. https://doi.org/10.1016/j.parkreldis.2016.09.012

Luszczki J, Wojcik-Cwikla J, Andres M J, Czuczwar S (2005). Pharmacological and Behavioral Characteristics of Interactions between Vigabatrin and Conventional Antiepileptic Drugs in Pentylenetetrazole-Induced Seizures in Mice: An Isobolographic Analysis. Neuropsychopharmacology, 30: 958-973.

Marie-Paule Austin, Cognitive deficits in depression Possible implications for functional neuropathology. The British Journal of Psychiatry (2001) 178: 200-206.

Marise B. Parent et al. Septohippocampal Acetylcholine: Involved in but not Necessary for Learning and Memory? Learn. Mem. 2004. 11: 9-20

Mark Rapaport, Future Drugs for the Treatment of Depression: The Need to Look Beyond Monoamine Systems. Primary Psychiatry. 2009; 16:3(Suppl 3): 14-16.

Masatomo Ishikawa and Kenji Hashimoto Journal of Receptor, Ligand and Channel Research 2009.

Maurice T, Privat A. SA4503, a novel cognitive enhancer with sigma 1 receptor agonist properties, facilitates NMDA receptor-dependent learning in mice. Eur J Pharmacol 1997; 328(1):9-18.

McKhann G, Drachman D, Folstein M, Katzman R, Price D, Stadlan E M. Clinical diagnosis of Alzheimer's disease: report of the NINCDS-ADRDA Work Group under the auspices of Department of Health and Human Services Task Force on Alzheimer's Disease. Neurology (1984); 34 (7): 939-44

McKhann G M., Knopman D S., Chertkow H., Hyman B T., Jack C R. Jr., Kawas C H, Klunk W E, Koroshetz W J, Manly J, Mayeux R, Mohs R C, Morris J C, Rossor M N, Scheltens P, Carrillo M C., Thies B., Weintraub S., Phelps C H. The diagnosis of dementia due to Alzheimer's disease: Recommendations from the National Institute on Aging-Alzheimer's Association workgroups on diagnostic guidelines for Alzheimer's disease. Alzheimer's & Dementia (2011); 7(3):263-269 Alzheimer's Association, www.alz.org Newcomer J W, Krystal J H. NMDA receptor regulation of memory and behavior in humans. Hippocampus 2001; 11 (5):529-42.

Nilsson M, Carlsson A, Markinhuhta K R, Sonesson C, Pettersson F, Gullme M, et al. The dopaminergic stabiliser ACR16 counteracts the behavioural primitivization induced by the NMDA receptor antagonist MK-801 in mice: implications for cognition. Prog Neuropsychopharmacol Biol Psychiatry 2004; 28:677-85.

Onaolapo O et al. Elevated Plus Maze and Y-Maze Behavioral Effects of Subchronic, Oral Low Dose Monosodium Glutamate in Swiss Albino Mice IOSR Journal of Pharmacy and Biological Sciences, Volume 3, Issue 4 (September-October 2012), PP 21-27.

Parada-Turska J, Turski W A. Excitatory amino acid antagonists and memory: effect of drugs acting at N-methyl-D-aspartate receptors in learning and memory tasks. Neuropharmacology 1990; 29(12): 1111-6.

Petrella, J. R., Sheldon, F. C., Prince, S. E., Calhoun, V. D., & Doraiswamy, P. M. (2011). Default mode network connectivity in stable vs progressive mild cognitive impairment. Neurology, 76(6), 511-517. https://doi.org/10.1212/WNL.0b013e31820af94e Pike C J, Walencewicz A J, Glabe C G, Cotman C W. In vitro aging of beta-amyloid protein causes peptide aggregation and neurotoxicity. Brain Res. (1991); 563(1-2):311-4.

Sahlholm K et al Molecular Psychiatry (2013).

Sakono M1, Zako T. Amyloid oligomers: formation and toxicity of Abeta oligomers. FEBS J. (2010) March; 277(6):1348-58.

Sambataro, F., Murty, V. P., Callicott, J. H., Tan, H. Y., Das, S., Weinberger, D. R., & Mattay, V. S. (2010). Age-related alterations in default mode network: Impact on working memory performance. Neurobiology of Aging, 31(5), 839-852.

Saunders J A, Gandal M J, Roberts T P, Siegel S J. NMDA antagonist MK801 recreates auditory electrophysiology disruption present in autism and other neurodevelopmental disorders. Behavioural brain research 2012; 234(2): 233-237.

Selkoe D J. Alzheimer's disease: genes, proteins, and therapy. Physiol Rev (2001); 81: 741-766.

Shang-Yi Tsaia et al, PNAS 2009.

Sisodia S S, Koo E H, Beyreuther K, Unterbeck A, Price D L. Evidence that beta-amyloid protein in Alzheimer's disease is not derived by normal processing. Science. (1990); 248(4954):492-5.

Stafstrom C E, Tandon P, Hori A, Liu Z, Mikati M A, Holmes G L., Acute effects of MK801 on kainic acid-induced seizures in neonatal rats. Epilepsy Res. 1997 January; 26(2):335-44.

Steen R G et al., Cognitive deficits in children with sickle cell disease. J Child Neurol. 2005 February; 20(2):102-7.

Stone M, Gabrieli J D, Stebbins G T, and Sullivan E V. Working and strategic memory deficits in schizophrenia. Neuropsychology 1998; 12(2):278-88.

van den Buuse M, Garner B, Gogos A, and Kusljic S. Importance of animal models in schizophrenia research. Aust N Z J Psychiatry 2005 July; 39(7):550-7.

van Rijckevorsel K, Cognitive problems related to epilepsy syndromes, especially malignant epilepsies. (2006) Seizure, 15 (4), pp. 227-234.

Weinberger D R, Gallhofer B. Cognitive function in schizophrenia. int Clin Psychopharmacol 1997; 12(Suppl 4): S29-36.

Winkler J, et al., Essential role of neocortical acetylcholine in spatial memory. Nature 375, 484-487 (8 Jun. 1995).

Yagasaki et al, J Biol Chem, 2006.

Yasuo Miki et al, Neuropathology 2014; 34, 148-158.

Yuxiang Xie, Michael R. Hayden, and Baoji Xu, BDNF Overexpression in the Forebrain Rescues Huntington's Disease Phenotypes in YAC128 Mice, J Neurosci. 2010 Nov. 3; 30(44): 14708-14718.

Zeynep Ates-Alagoz and Adeboye Adejare, NMDA Receptor Antagonists for Treatment of Depression. Pharmaceuticals 2013, 6, 480-499.

Zhou, J., Greicius, M. D., Gennatas, E. D., Growdon, M. E., Jang, J. Y., Rabinovici, G. D., . . . Seeley, W. W. (2010). Divergent network connectivity changes in behavioural variant frontotemporal dementia and Alzheimer's disease. Brain, 133(5), 1352-1367. https://doi.org/10.1093/brain/awq075

What is claimed is:

1. A method of improving memory or attention in a human subject comprising administering to the subject a composition comprising pridopidine or a pharmaceutically acceptable salt thereof wherein the memory or attention is associated with default mode network (DMN) dysfunction.

2. The method of claim 1, wherein memory is short term memory, long term memory or working memory.

3. The method of claim 1, wherein the subject is afflicted with a cognitive deficit.

4. The method of claim 1, wherein the subject is prone to or predisposed to have a cognitive deficit.

5. The method of claim 3, wherein the cognitive deficit is a memory deficit.

6. The method of claim 5, wherein the memory deficit is a short-term memory deficit or memory loss.

7. The method of claim 6, wherein the memory loss is caused by one or more of age-related changes in memory, mild cognitive impairment, dementia or depression.

8. The method of claim 3, wherein the cognitive deficit is caused by or associated with a disease or disorder.

9. The method of claim 8, wherein the disease or disorder is selected from the group consisting of Huntington's disease (HD), epilepsy, Mild cognitive impairment (MCI), Parkinson's disease, Alzheimer's disease, dementia associated with Lewy Bodies and Creutzfeldt-Jacob disease.

10. The method of claim 1, wherein the amount of pridopidine or a pharmaceutically acceptable salt thereof is administered to the human subject once daily, 2-4 times a day, less than once a day, or 2-4 times per week.

11. The method of claim 1, wherein the amount of pridopidine administered is between 1 mg/day-315 mg/day, 22.5 mg/day-315 mg/day, or 90 mg/day-315 mg/day.

12. The method of claim 1, wherein the amount of pridopidine is administered orally, parenterally, intravascularly, paracancerally, transmucosally, transdermally, intramuscularly, intranasally, intravenously, intradermally, subcutaneously, sublingually, intraperitoneally, intraventricularly, intracranially, intravaginally, by inhalation, rectally, or intratumorally.

13. The method of claim 1, wherein the pharmaceutically acceptable salt of pridopidine is pridopidine hydrochloride, hydrobromide, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methanesulphonate, naphthalene-2-sulphonate, phthalate, salicylate, sorbate, stearate, succinate, tartrate or toluene-p-sulphonate salt.

14. The method of claim 1, further comprising the administration of a psychiatric drug, an antidepressant drug, anxiolytics, antipsychotic medications or combination thereof.

15. The method of claim 14, wherein the antidepressant is selected from the group consisting of citalopram, fluoxetine, paroxeine, sertraline, and trazodone.

16. The method of claim 14, wherein the anxiolytic is selected from the group consisting of lorazepam and oxazepam.

17. The method of claim 14, wherein the antipsychotic medication is selected from the group consisting of aripiprazole, clozapine, haloperidol, olanzapine, quetiapine, risperidone, and ziprasidone.

* * * * *